(12) United States Patent
Kedrowski et al.

(10) Patent No.: US 11,931,451 B2
(45) Date of Patent: Mar. 19, 2024

(54) SKIN LIGHTENING COMPOUNDS FROM FRUIT SEED EXTRACTS

(71) Applicants: WiSys Technology Foundation, Inc., Madison, WI (US); Botanic Innovations, LLC, Spooner, WI (US)

(72) Inventors: Brant Lawrence Kedrowski, Oshkosh, WI (US); Mark J. Mueller, Spooner, WI (US)

(73) Assignees: WiSys Technology Foundation, Inc., Madison, WI (US); Botanic Innovations, LLC, Spooner, WI (US)

( * ) Notice: Subject to any disclaimer, the term of this patent is extended or adjusted under 35 U.S.C. 154(b) by 0 days.

(21) Appl. No.: 16/322,241

(22) PCT Filed: Aug. 1, 2017

(86) PCT No.: PCT/US2017/044975
§ 371 (c)(1),
(2) Date: Jan. 31, 2019

(87) PCT Pub. No.: WO2018/026859
PCT Pub. Date: Feb. 8, 2018

(65) Prior Publication Data
US 2019/0192417 A1    Jun. 27, 2019

Related U.S. Application Data

(60) Provisional application No. 62/369,651, filed on Aug. 1, 2016.

(51) Int. Cl.
*A61K 8/9783* (2017.01)
*A61K 8/02* (2006.01)
(Continued)

(52) U.S. Cl.
CPC ............ *A61K 8/9783* (2017.08); *A61K 8/022* (2013.01); *A61K 8/062* (2013.01); *A61K 8/498* (2013.01); *A61K 8/9789* (2017.08); *A61Q 19/02* (2013.01)

(58) Field of Classification Search
CPC .... A61K 8/9783; A61K 8/9789; A61K 8/022; A61K 8/062; A61K 8/498; A61Q 19/02
See application file for complete search history.

(56) References Cited

U.S. PATENT DOCUMENTS

2006/0251753 A1   11/2006  Alkayali
2006/0280819 A1   12/2006  Alkayali
(Continued)

FOREIGN PATENT DOCUMENTS

EP    0294808 A1   12/1988
EP    1967078 A1    9/2008
(Continued)

OTHER PUBLICATIONS

Parry et al, Chemical Compositions, Antioxidant Capacities, and Antiproliferative Activities of Selected Fruit Seed Flours, 2006, J. Agric. Food Chem., 54, pp. 3773-3778. (Year: 2006).*

(Continued)

*Primary Examiner* — Trevor Love
(74) *Attorney, Agent, or Firm* — Schwegman Lundberg & Woessner, P.A.

(57) ABSTRACT

The disclosure provides a method of isolating one or more compounds present in fruit seed extracts that have anti-tyrosinase or whitening activity, compositions having one or more fruit seed extracts that have anti-tyrosinase or whitening (lightening) activity.

11 Claims, 25 Drawing Sheets

(51) Int. Cl.
  A61K 8/06    (2006.01)
  A61K 8/49    (2006.01)
  A61K 8/9789   (2017.01)
  A61Q 19/02   (2006.01)

(56) References Cited

U.S. PATENT DOCUMENTS

| | | | |
|---|---|---|---|
| 2007/0014882 | A1 | 1/2007 | Feldman |
| 2010/0239553 | A1 | 9/2010 | Bartunek et al. |
| 2011/0123471 | A1* | 5/2011 | Rana ............ A61K 8/9767 424/62 |
| 2013/0337092 | A1 | 12/2013 | Konda et al. |
| 2014/0004214 | A1* | 1/2014 | Kedrowski .......... A61K 31/353 424/732 |
| 2014/0295008 | A1 | 10/2014 | Wishnick et al. |
| 2015/0079208 | A1 | 3/2015 | Bates et al. |

FOREIGN PATENT DOCUMENTS

| | | |
|---|---|---|
| FR | 2255055 | 7/1975 |
| WO | WO-2005097106 A1 | 10/2005 |
| WO | WO-2006068759 A2 | 6/2006 |
| WO | WO-2010076913 A1 | 7/2010 |
| WO | WO-2013090715 A1 | 6/2013 |
| WO | WO-2018026859 A1 | 2/2018 |

OTHER PUBLICATIONS

"International Application Serial No. PCT/US2017/044975, International Search Report dated Oct. 10, 2017", 5 pgs.
"International Application Serial No. PCT/US2017/044975, Written Opinion dated Oct. 10, 2017", 8 pgs.
"Canadian Application Serial No. 3,036,504, Response filed Aug. 6, 2020 to Office Action dated Apr. 9, 2020", 79 pages.
"Canadian Application Serial No. 3,036,504, Office Action dated Apr. 9, 2020", 4 pages.
"Canadian Application Serial No. 3,036,504, Office Action dated Jan. 22, 2021", 5 pgs.
Aqil, F, et al., "Antioxidant and antiproliferative activities of anthocyanin/ellagitannin-enriched extracts from *Syzygium cumini* L. ('jamun', the Indian Blackberry)", Nutr Cancer, (64(3), pp. 428-438, (Apr. 2012), 21 pgs.
Aslam, Muhammad, et al., "Pomegranate as a cosmeceutical source: Pomegranate fractions promote proliferation and procollagen synthesis and inhibit matrix metalloproteinase-1 production in human skin cells", Journal of Ethnopharmacology 103, (2006), 311-318.
Chen, Jinyu, et al., "(Abstract) Screening of Key Antioxidant Compounds of Longan (*Dimocarpus longan* Lour.) Seed Extract by Combining Online Fishing/Knockout, Activity Evaluation, FT-ICR-MS and HPLC-ESI-MS Methods.", J Agric Food Chem, (2014), 1 pg.
Chen, Jinyu, et al., (Abstract) "Screening Key Antioxidant Compounds Longan Seed Extract Combining Online Fishing/Knockout, Activity Evaluation, Fourier Transform Ion Cyclotron Resonance Mass Spectrometry, & High-Perf. Liquid Chromatography Electrospray ionization mass spectrometry methods", J Agric Food Chem 62(40), (2014), 1 pg.
Cho, H, et al., "Chemopreventive activity of ellagitannins and their derivatives from black raspberry seeds on HT-29 colon cancer cells", Food and Function, 6/5, (May 1, 2015), 1675-1683.
Godevac, D, et al., "Blackberry Seed Extracts and Isolated Polyphenolic Compounds Showing Protective Effect on Human Lymphocytes DNA", Journal of Food Science, 76/7, (Aug. 8, 2011), C1039-C1043.
Hsu, Cheng-Kuang, et al., "(Abstract) Crude ethanol extracts from grape seeds and peels exhibit anti-tyrosinase activity", J Cosmet Sci 63(4), (2012), 1 pg.
Hussain, Shahzad, et al., "(Abstract) Review: an exposition of medicinal preponderance of *Moringa oleifera* (Lank.)", Pak J Pharm Sci 27(2), (2014), 1 pg.

Hussain, Shahzad, et al., "An exposition of medicinal preponderance of *Moringa oleifera* (Lank.)", Pak. J. Pharm. Sci., vol. 27, No. 2,, (Mar. 2014), 397-403.
Kedrowski, Brant, "(Abstract & Poster) Tyrosinase inhibitors from seed meal extracts: applications for skin whitening and skin tone evening agents", Poster presentation at the 2016 UW System Chemistry Faculties Meeting, (Oct. 28-29, 2016), 1 pg.
Kowalczyk, M, et al., "Differential effects of several phytochemicals and their derivatives on murine keratinocytes in vitro and in vivo: Implications for skin cancer prevention", Carcinogenesis vol. 30, No. 6, (2009), 1008-1015.
Kowalczyk, M, et al., "Synergistic effects of combined phytochemicals and skin cancer prevention in SENCAR mice", Cancer Prev Res; 3(2), (2010), 170-178.
Navarro, Marta, et al., "(Abstract) An aqueous pomegranate seed extract ameliorates oxidative stress of human hepatoma HepG2 cells", J Sci Food Agric, (2014), 1 pg.
Panyathep, Atita, et al., "(Abstract) Effects of dried longan seed (*Euphoria longana* Lam.) extract on VEGF secretion and expression in colon cancer cells and angiogenesis in human umbilical vein endothelial cells", Journal of Functional Foods, 5(3), (2013), 1 pg.
Panyathep, Atita, et al., "Antioxidant and anti-matrix metalloproteinases activities of dried longan (*Euphoria longana*) seed extract", ScienceAsia 39, (2013), 12-18.
Rangkadilok, N, et al., "(Abstract) Identification and Quantification of Polyphenolic Compounds in Longan (*Euphoria longana* Lam.) Fruit", J Agric Food Chem 53(5), (2005), 1 pg.
Rangkadilok, N., et al., "In vitro antifungal activities of longan (*Dimocarpus longan* Lour.) seed extract", Fitoterapia 83(3), (2012), 1 pg.
Sagdic, Osman, et al., "Interaction Between Some Phenolic Compounds and Probiotic Bacterium in Functional Ice Cream Production", Food and Bioprocess Technology, 5(8), (2012), 2964-2971.
Vekiari, S, et al., "(Abstract) Extraction and determination of ellagic acid content in chestnut bark and fruit", Food Chem 110(4), (2008), 1 pg.
Winand, Julie, et al., "(Abstract) The anti-inflammatory effect of a pomegranate husk extract on inflamed adipocytes and macrophages cultivated independently, but not on the inflammatory vicious cycle between adipocytes and macrophages", Food Funct. 5(2), (2014), 1 pg.
Wu, Dan, et al., "(Abstract) Pomegranate husk extract, punicalagin and ellagic acid inhibit fatty acid synthase and adipogenesis of 3T3-L1 adipocyte", Journal of Functional Foods, vol. 5, Issue 2, (2013), 1 pg.
Zhang, L, et al., "(Abstract) Quantification of Gallic Acid and Ellagic Acid from the Seed of Cornus officinalis by UHPLC Method and Their Antioxidant Activity", Chemical Engineering Communications, (2014), 1 pg.
"Canadian Application Serial No. 3,036,504, Response filed May 21, 2021 to Office Action dated Jan. 22, 2021", 18 pgs.
Yoshimura, Mineka, et al., "Inhibitory effect of an ellagic acid-rich pomegranate extract jon tyrosinase activity and ultraviolet-induced pigmentation", Bioscience Biotechnology Biochemistry, Japan Society for Bioscience, Biotechnology and Agrochemistry, Tokyo, Japan, vol. 29, No. 12, (Dec. 1, 2005), 6 pages.
"Canadian Application Serial No. 3,036,504, Office Action dated Sep. 15, 2021", 5 pages.
Park, Miyoung, et al., "Antioxidant and Anti-Inflammatory Activities of Tannin Fraction of the Extract from Black Raspberry Seeds Compared to Grape Seeds", Journal of Food Biochemistry, 38, (2014), 259-270.
"Canadian Application Serial No. 3,036,504, Response filed Jan. 14, 2022 to Office Action dated Sep. 15, 2021", 15 pages.
"Canadian Application Serial No. 3,036,504, Non Final Office Action dated Mar. 11, 2022", 5 pages.
"Canadian Application Serial No. 3,036,504, Examiner's Rule 86(2) Report dated Oct. 26, 2022", 4 pgs.
"Canadian Application Serial No. 3,036,504, Response filed Jul. 6, 2022 to Non Final Office Action dated Mar. 11, 2022", 12 pgs.
"Canadian Application Serial No. 3,036,504, Office Action dated May 5, 2023", 4 pgs.

(56) References Cited

OTHER PUBLICATIONS

"Canadian Application Serial No. 3,036,504, Response filed Feb. 16, 2023 to Examiner's Rule 86(2) Report dated Oct. 26, 2022", 24 pgs.
"Canadian Application Serial No. 3,036,504, Response filed Aug. 31, 2023 to Office Action dated May 5, 2023", 22 pgs.

* cited by examiner

Fig. 10

% Inhibition [(blank rate − inhibitor rate)/(blank rate)]*100

| Concentration (mg/mL) | Known Inhibitors | | | | | | | Fruit Seed Extracts | | | | | | | | | Vegetable Seed Extracts | | | | |
|---|---|---|---|---|---|---|---|---|---|---|---|---|---|---|---|---|---|---|---|---|---|
| | kojic acid | alpha-arbutin | b-arbutin | Presperse arbutin | hydroquinone | BASF Radiaskin | quercetin* | cranberry | cranberry skins | pomegranate | red raspberry | red raspberry 2h extraction | black raspberry | blackberry | blueberry | watermelon | radish | tomato | broccoli | carrot** | red raspberry and tomato § |
| 0.001 | 33 | 0 | 0 | 11 | 0 | 11 | 0 | 3.7 | 1 | 0 | 0 | 3 | 0 | 3.7 | 0 | −2 | −4 | −2 | −5 | −2 | 10 |
| 0.01 | 85 | 26 | 28 | 33 | 38 | 19 | 44 | 3.4 | 4 | 7.4 | 28 | 6 | 26 | 19 | 18 | 4 | 0 | 20 | 1 | 11 | 32 |
| 0.1 | 100 | 56 | 52 | 56 | 63 | 44 | 100 | 48 | 52 | 21 | 79 | 21 | 78 | 74 | 74 | 33 | 19 | 55 | 33 | | 78 |
| 1 | 100 | | | | | 52 | | | | 62 | | 79 | | | | | | | | | |

*saturated at 0.1 mg/mL and higher concentrations
**insoluble at 1 mg/mL
§ both red raspberry and tomato were present at the listed concentrations

| | PHASE ONE | |
|---|---|---|
| SOLVENT | ADDED TO 1.0G RSE (G) | RESULT |
| METHANOL | 10.0 | METHANOL TOOK ON DARK COLOR FROM RSE RAPIDLY AFTER INITIAL ADDITION OF SOLVENT. MANY SOLIDS LEFT UNDISSOLVED. AFTER ~5 MINUTES OF CONTACT TIME AND INTERMITTENT MIXING, COLOR WAS COMPLETELY STRIPPED FROM UNDISSOLVED SOLIDS, LEAVING ALMOST COMPLETELY WHITE PARTICULATES AT BOTTOM OF VESSEL. |
| ETHANOL | 10.0 | SEE METHANOL: DIFFERENCE BETWEEN METHANOL AND ETHANOL WAS SLOWER TO EXTRACT COLOR FROM SOLIDS |
| PROPYLENE GLYCOL | 10.0 | VERY DARK LIQUID PRODUCED WITHIN ~5 MINUTES OF CONTACT TIME, EVIDENCE OF DISSOLUTION INTO SOLVENT. SOLIDS WERE EVIDENT AFTER ~1 HOUR OF CONTACT TIME WITH INTERMITTENT MIXING. |
| PROPANEDIOL | 10.0 | SEE PROPYLENE GLYCOL: DIFFERENCE BETWEEN PROPYLENE GLYCOL AND PROPANEDIOL WAS SLOWER EXTRACTION TIME OF COLOR FROM RSE. |
| GLYCERIN | 10.0 | SEE PROPANEDIOL: A DIFFERENCE BETWEEN PROPANEDIOL AND GLYCERIN WAS SLOWER EXTRACTION TIME OF COLOR FROM RSE. |
| 200 GRAIN VINEGAR | 10.0 | CLOSE TO COMPLETE RSE SOLUBILIZATION IN SOLUTION AFTER 1 MINUTE OF MIXING. DARK SOLUTION COLOR DEVELOPED IMMEDIATELY AFTER INITIAL CONTACT. VERY LITTLE TURBIDITY INITIALLY. |
| WATER | 10.0 | SLIM AMOUNT OF COLOR PRODUCED IN SOLUTION FROM RSE, ALMOST NO SOLUBILIZATION OF PARTICULATES COMPARED WITH APPROXIMATE VOLUME OF RSE ADDED. |
| SODIUM LAURYL ETHER SULFATE 60% | 10.0 | VERY SLOW TO DEVELOP ANY COLOR FROM THE RSE, SOMEWHAT SOLIDIFIED THE RSE ON BOTTOM OF VESSEL. LITTLE SOLID DISSOLVED AFTER ~1 HOUR AFTER INITIAL CONTACT |
| 50% CITRIC ACID SOLUTION | 10.0 | SEE 200 GRAIN VINEGAR: DIFFERENCE BETWEEN CITRIC ACID AND VINEGAR WAS THE SPEED IN WHICH THE DISSOLUTION OCCURRED. CITRIC ACID WAS SLOWER TO DISSOLVE RSE |
| HCL 0.1 N | 10.0 | VERY CLOSE TO A PERFECT COMBINATION OF OBSERVATIONS FROM PHASE 2 OF 200 GRAIN VINEGAR AND 50% CITRIC ACID SOLUTION WITHIN ~30 MINUTES OF CONTACT TIME. |
| LAURAMINE OXIDE 30% | 10.0 | ADVERSE REACTION, WHERE RSE HARDENED ON THE BOTTOM OF THE VESSEL. SOME COLOR WAS DEVELOPED, BUT CONSIDERED INCOMPATIBLE. |
| ISOPROPYL MYRISTATE | 10.0 | LITTLE TO NO INTERACTION. ACTED LIKE AN INERT SUSPENSION AGENT. |
| ISOPRENE GLYCOL | 10.0 | LITTLE TO NO INTERACTION. ACTED LIKE AN INERT SUSPENSION AGENT. |
| AVOCADO OIL | 10.0 | LITTLE TO NO INTERACTION. ACTED LIKE AN INERT SUSPENSION AGENT. |

*Fig. 15A*

| FIG. 15A | FIG. 15B |
|---|---|

| PHASE TWO | |
|---|---|
| ADDED TO PHASE ONE SOLUTION (G) | RESULT |
| 200 GRAIN VINEGAR: 3.0G | ~75% OF THE SOLIDS LEFT FROM PHASE 1 WERE SOLUBILIZED. VERY SLIGHT SOLUTION TURBIDITY. |
| 200 GRAIN VINEGAR: 3.0G | ALL SOLIDS WERE DISSOLVED, BUT AN OILY SUBSTANCE PRECIPITATED OUT OF SOLUTION AND STUCK TO BOTTOM OF VESSEL. |
| 200 GRAIN VINEGAR: 3.0G | ALL SOLIDS WERE DISSOLVED. SLIGHT WISPS NOTED IN SOLUTION, ALTHOUGH NO TURBIDITY WAS OBSERVED. MAY HAVE SLIGHT SOLUTION INCOMPATIBILITY |
| 200 GRAIN VINEGAR: 3.0G | ALL SOLIDS WERE DISSOLVED. EXTREMELY SLIGHT SOLUTION TURBIDITY. |
| 200 GRAIN VINEGAR: 3.0G | NO LARGE GRANULES OBSERVED, BUT A FINE SEDIMENT LAYER FOUND AT THE BOTTOM OF THE VESSEL. |
| 200 GRAIN VINEGAR: 3.0G | MOST SOLIDS WERE ABLE TO BE DISSOLVED WITH THE ADDITIONAL VINEGAR ADDED; DISSOLUTION WITHIN 10 MINUTES. AFTER ~12 HOURS OF INITIAL ADDITION OF VINEGAR, SOLUTION BECAME MODERATE TO VERY TURBID. LARGE DEPOSITS OF UNDISSOLVED MATERIAL WERE FOUND STUCK TO BOTTOM OF VESSEL. |
| CITRIC ACID ANHYDROUS: 0.2G | VERY LITTLE CHANGE WAS OBSERVED COMPARED TO PHASE 1. |
| NA (ADDITIONAL TIME TO REACT) | AFTER 12 HOURS OF CONTACT TIME, MIXING ONLY FOR THE FIRST ~1 HOUR INTERMITTENTLY, ALL SOLIDS FULLY DISSOLVED AND COLOR IS DEEP, LITTLE TO NO TURBIDITY. |
| NA (ADDITIONAL TIME TO REACT) | AFTER ~12 HOURS OF INITIAL ADDITION OF CITRIC ACID SOLUTION TO RSE, SOLUTION BECAME EXTREMELY TURBID. NO DEPOSITS OF UNDISSOLVED MATERIAL WERE FOUND STUCK TO BOTTOM OF VESSEL, BUT FINE, SILT LIKE PARTICULATES FOUND AT HIGH CONCENTRATION IN SOLUTION. |
| NA (ADDITIONAL TIME TO REACT) | NO CHANGE OBSERVED. |
| NA (ADDITIONAL TIME TO REACT) | NO CHANGE OBSERVED. |
| NA (ADDITIONAL TIME TO REACT) | NO CHANGE OBSERVED. |
| NA (ADDITIONAL TIME TO REACT) | NO CHANGE OBSERVED. |
| NA (ADDITIONAL TIME TO REACT) | NO CHANGE OBSERVED. |

*Fig. 15B*

| MOISTURIZING SPRAY LIQUID | | |
|---|---|---|
| DESCRIPTION | % IN FORMULA | FUNCTION |
| ETHANOL | 50-80 | SOLVENT/CARRIER |
| RSE PREPARATION | 10-30 | ACTIVE/HUMECTANT |
| OCTYLDODECYL OLIVATE | 10-30 | EMOLLIENT |
| FRAGRANCE | 0.1-2 | SCENT |

| SERUM ANHYDROUS | | |
|---|---|---|
| DESCRIPTION | % IN FORMULA | FUNCTION |
| VEGETABLE/FRUIT/PLANT OIL | 10-90 | SOLVENT/CARRIER |
| RSE PREPARATION | 10-90 | ACTIVE/HUMECTANT |
| OCTYLDODECYL OLIVATE | 5-30 | EMOLLIENT |
| FRAGRANCE | 0.1-2 | SCENT |

| SERUM AQUEOUS | | |
|---|---|---|
| DESCRIPTION | % IN FORMULA | FUNCTION |
| WATER | 50-90 | SOLVENT/CARRIER |
| CARBOMER/XANTHAN GUM/GUAR GUM | 0.05-2 | STRUCTURANT/THICKENER |
| SODIUM HYALURONATE | 0.05-1 | HUMECTANT/STRUCTURANT |
| ESTER EMULSIFIER | 1-5 | EMULSIFIER |
| RSE PREPARATION | 10-30 | ACTIVE |
| BROAD SPECTRUM PRESERVATIVE | 0.5-2 | PRESERVATIVE |
| OCTYLDODECYL OLIVATE | 5-10 | EMOLLIENT |
| FRAGRANCE | 0.1-2 | SCENT |
| CITRIC ACID | 0-0.5 | PH ADJUSTOR/BUFFER |
| SODIUM HYDROXIDE | 0-0.5 | PH ADJUSTOR/BUFFER |

*Fig. 16A*

| O/W EMULSION | | |
|---|---|---|
| DESCRIPTION | % IN FORMULA | FUNCTION |
| WATER | 50-80 | SOLVENT/CARRIER |
| FATTY ALCOHOL | 2-5 | EMULSIFIER |
| FATTY ACID | 2-5 | EMULSIFIER |
| RSE PREPARATION | 5-20 | ACTIVE/HUMECTANT |
| OCTYLDODECYL OLIVATE | 1-5 | EMOLLIENT |
| BROAD SPECTRUM PRESERVATIVE | 0.5-2 | PRESERVATIVE |
| FRAGRANCE | 0.1-2 | SCENT |
| CITRIC ACID | 0-0.5 | PH ADJUSTOR/BUFFER |
| SODIUM HYDROXIDE | 0-0.5 | PH ADJUSTOR/BUFFER |

| EXEMPLARY EMOLLIENTS OPTIONS |
|---|
| ISOPROPYL MYRISTATE |
| CAPRYLIC/CAPRIC TRIGLYCERIDES |
| OCTYLDODECYL OLIVATE |
| UNDECANE & TRIDECANE |
| CAPRYLYL-CAPRYLATE / CAPRATE |
| EATERS (SHEA BUTTER ETHYL ESTER) |
| ETHYL ESTERS (CLASS OF COMPOUNDS) |

| EXEMPLARY EMULSIFIERS OPTIONS |
|---|
| LECITHIN (HYDROGENATED LECITHIN) |
| POLYGLYCERYL-10 PENTASTEARATE |
| BEHENOYL ALCOHOL |
| SODIUM STEAROYL LACTYLATE |
| CETYL ALCOHOL |
| STEARIC ACID |
| CETEARYL ALCOHOL |
| ESTERS |

Fig. 16B

SKIN LIGHTENING COMPOUNDS FROM FRUIT SEED EXTRACTS

CROSS-REFERENCE TO RELATED APPLICATIONS

This application is a U.S. National Stage Application filed under 35U.S.C. §. 371 from International Application Serial NO. PCT/US2017/044975, filed on Aug. 1, 2017, and published as WO 2018/026859 on Feb. 8, 2018, which claims the benefit of priority to U.S. Provisional Application Ser. No. 62/369,651, filed on Aug. 1, 2016, the disclosures of which are incorporated by reference herein in their entireties.

BACKGROUND

There is a significant world market for skin whitening and skin tone evening cosmetic agents to reduce hyperpigmentation from age spots, melasma, sun exposure, freckles, and for general complexion lightening. The current market leading product is the synthetic chemical bleaching agent hydroquinone. While effective, the safety of hydroquinone has been called into question. It has been banned in a number of overseas markets and could soon be banned in the US as well. There is strong commercial potential for safe and effective alternatives to hydroquinone.

SUMMARY

This disclosure provides methods of providing extracts from seed flours of raspberries and other fruits or vegetables or other botanicals having materials that are enriched in certain compounds, e.g., the compound ellagic acid and/or other related compounds including ellagitannins. Ellagic acid and its derivatives have commercial potential for use in topical skin treatments for skin whitening and wrinkle reduction. In one embodiment, compositions enriched in ellagic acid, ellagitannin, or derivatives thereof, are useful in cosmetic applications. In one embodiment, the compositions include a natural source of ellagic acid ("from raspberry seeds") which may provide for higher concentration of ellagic acid than current methods, which compositions may also include other compounds, and so result in higher efficacy, e.g., to reduce hyperpigmentation from age spots, melasma, freckles, and for general complexion lightening.

As described herein, skin whitening and skin tone evening agents may be obtained from seed meal extracts. Thus, the extracts may be employed to inhibit, prevent or reduce hyperpigmentation from age spots, melasma, freckles, and for general complexion lightening. In one embodiment, the extracts inhibit the enzyme tyrosinase, which is a key catalyst in the production of melanin. The tyrosinase inhibiting ability of extracts from blackberry, blueberry, broccoli, carrot, cranberry, grape (chardonnay and red), pomegranate, pumpkin, radish, raspberry (red and black), tomato, and watermelon was tested and compared to known inhibitors and commercial skin whitening products. Several of the seed extracts compared favorably with these known inhibitors and a few even exceeded their potency at concentrations of 1 mg/mL. The seed meal extracts were also characterized by high performance liquid chromatography with diode array UV-visible detection as well as by Matrix-Assisted Laser Desorption/Ionization Time-of-Flight Mass Spectrometry. Many of the tested fruit seed extracts had high levels of the molecule ellagic acid. Although ellagic acid is highly insoluble, the presence of other compounds in the fruit seed meals may assist in solubilizing ellagic acid to improve its effectiveness in water-based media. Cold pressed seed meal powders were obtained with yields of about 7 to about 18%, powders of blackberry, blueberry, broccoli, carrot, chia, cranberry, grape (Chardonnay and red), pomegranate, pumpkin, radish, raspberry (red and black), tomato or watermelon may be employed. The tyrosinase activity may be monitored by combining the extract with L-DOPA, and also in parallel optionally with a solution of known inhibitor (or blank), and formation of L-dopachrome measured over time by UV absorbance.

In one embodiment, the extract includes ellagic acid:

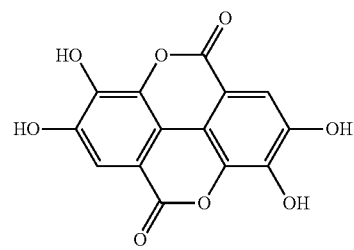 [SMILES: O=c1oc2c(O)c(O)cc3c(=O)oc4c(O)c(O)cc1c4c23]

In one embodiment, the extract for use in the compositions and methods does not include one or more of the following: Vitamin E, tocopherols, tocotrinols, carotinods, polyunsaturated fatty acids, sterols, amino acids, or carbohydrates.

The invention thus provides a method to isolate compounds in fruit or fruit seed extracts, such as red raspberry, black raspberry, or blueberry extracts, that have anti-tyrosinase or skin whitening activity, or both, or that include ellagic acid, ellagitannins, or derivatives thereof. The method includes subjecting extracts, e.g., fruit seed extracts such as those from raspberries or grapes, to one or more separation techniques, and optionally identifying, and isolating subtractions with anti-tyrosinase activity, skin whitening activity, ellagic acid or a derivative thereof, or ellagitannins, and optionally repeating separation and identification/isolation steps using different parameters, so as to isolate fractions having a plurality of desired individual compounds, or substantially pure fractions having individual chemical compounds, responsible for anti-tyrosinase or skin whitening activity. In embodiment, the fruit seed extract is a cold press extract which yields small amounts of seed oils and high amounts of seed meal, which are rich in phytochemicals, e.g., 16 pounds of raspberry seeds generally yields 1 teaspoon of oil. In one embodiment cold pressed seed meals are dissolved or resuspended so that compounds are extracted into the solvent and the mixture is separated, e.g., compounds in the solvent are collected, and the solvent removed.

In one embodiment, a method to isolate compounds having anti-tyrosinase activity is provided. The method includes providing a cold press fruit seed extract dissolved or suspended in water to provide a first mixture. A lower alcohol is combined with the first mixture to provide a second mixture that allows for extraction of compounds including ellagic acid or an ellagitannin. Then the extracted compounds are separated to provide for a fraction that is enhanced in ellagic acid or ellagitannin and has anti-tyrosinase activity.

In one embodiment, a method to isolate ellagic acid or ellagitannin from fruit or vegetable seed extracts is provided. In one embodiment, the method includes providing a raspberry, blackberry or blueberry seed extract suspended in water, a lower alcohol or a water-lower alcohol mix, thereby providing a mixture. The mixture is incubated under conditions that allow for extraction of compounds including ellagic acid or ellagitannin and the extracted compounds are separated to provide for a fraction that is enhanced in ellagic acid or ellagitannin. In one embodiment, the water is at a pH greater than 8.

In one embodiment, the lower alcohol is propanol, butanol, ethanol or methanol. In one embodiment, the water lower alcohol mixture comprises 70:30 methanol:water. In one embodiment, the fraction inhibits eumelanin or phenmelanin production in human skin. In one embodiment, the extract is a powder. In one embodiment, the separation comprises filtering the mixture. In one embodiment, the separation includes subjected the mixture to separation on a C8 column, a C18 solid phase extraction column or an ion exchange chromatography column, or any combination thereof. In one embodiment, the separation includes subjecting the mixture to high pressure liquid chromatography. In one embodiment, the seed extract is a raspberry, blackberry, blueberry or pomegranate seed extract. In one embodiment, a fraction obtained by the method is provided.

Further provided is a use of the fraction in a dietary supplement, nutraceutical, or cosmetic formulation. For example, the fraction may be employed in a formulation such as a lotion, cream, serum, solid or gel for preventing, inhibiting or treating hyperpigmentation.

In one embodiment, to prepare a pharmaceutical composition, e.g., for topical application, a fruit seed extract is solubilized in a solvent, such as a polar solvent, e.g., methanol, ethanol, propanediol or propylene glycol, optionally using agitation. In one embodiment, the ratio of solid extract to solvent is about 1:20, e.g., 1:2, 1:5, 1:10 or 1:15. Then undissolved particulates are removed from the solution, e.g., using centrifugation or filtration. Optionally, the solvent, e.g., methanol, may be removed via evaporation using reduced pressure, and the resulting solid dissolved in a liquid carrier, e.g., ethanol, propanediol or propylene glycol.

In one embodiment, to formulate the active ingredient into a cosmetic preparation that diffuses into the skin, the formulation may include a light moisturizing liquid spray using solubilized extract, e.g., solubilized with alcohol, and compatible emollients such as caprylic, capric triglyceride, isopropyl myristate, or other light oils or esters. In one embodiment, the formulation may include an oil in water emulsion using propanediol as a carrier added to water phase. In one embodiment, the formulation may include liquid or gel serum using polar solvent carrier(s), emollients, and/or viscosity modifier(s). Additional optional ingredients include a suitable preservative system to prevent growth of bacteria, yeasts and/or molds, and/or an antioxidant(s) to prevent oxidation.

Generally, a "substantially pure" composition will comprise more than about 80% of a single macromolecular species present in the composition, e.g., more than about 85%, about 90%, about 95%, and about 99%, and in one embodiment, the object species is purified to essential homogeneity (contaminant species cannot be detected in the composition by conventional detection methods) wherein the composition consists essentially of a single macromolecular species. In one embodiment, a substantially pure fraction is one where a single compound represents at least 95% all macromolecular species present in the composition. In one embodiment, an isolated fraction is one where a single (first) compound represents at least 50%, or at least 60%, 70%, 80%, 90%, or any integer between 60 and 100, of all macromolecular species in the fraction but other compounds in the fraction individually or in combination with the first compound provide for anti-microbial activity. In one embodiment, chromatographic methods were used to separate the multitude of compounds present in fruit seed extracts into several fractions, each containing a simpler mixture of compounds. For example, high performance liquid chromatography (HPLC) and/or solid phase extraction (SPE) may be used to separate these complex mixtures. In one embodiment, simulated moving bed chromatography (SMBC) may be employed to separate mixtures. Thus, one type of separation method may be employed once, or two or more different types of separation methods may be employed in succession. In one embodiment, one type of chromatography column may be employed individually or in tandem, or two or more different types of columns may be employed sequentially or in tandem. The compounds displaying activity may then be purified in larger quantities, e.g., using the methods to identify those compounds which may include eliminating one or more steps, or through SMBC technology, and the resulting compositions may be employed as a cosmetic, nutraceutical or a pharmaceutical in compositions, e.g., in gel, cream, lotion, powder, tablet or liquid formulations. The structure of the compounds may be determined using proton nuclear magnetic resonance spectroscopy ($^1$H NMR), MALDI-TOF mass spectrometry, Ultra High Performance Liquid Chromatography (UPLC)-Quadrupole/Time of Flight (Q-TOF) mass spectrometry, and/or ultraviolet (UV) spectroscopy.

Thus, the invention provides compounds, isolated from fruit seed extracts, as well as compositions having that compound, for use in applications including cosmetic applications. In one embodiment, the invention provides a composition comprising an isolated fraction of a fruit seed extract having ellagic acid and optionally a pharmaceutically acceptable carrier. In one embodiment, the composition is a gel, serum or cream.

BRIEF DESCRIPTION OF THE FIGURES

FIG. 15. Solubility data for RSE (raspberry seed extract).

FIG. 16. Exemplary formulations.

DETAILED DESCRIPTION

Exemplary Separation Methods

Figure 1:
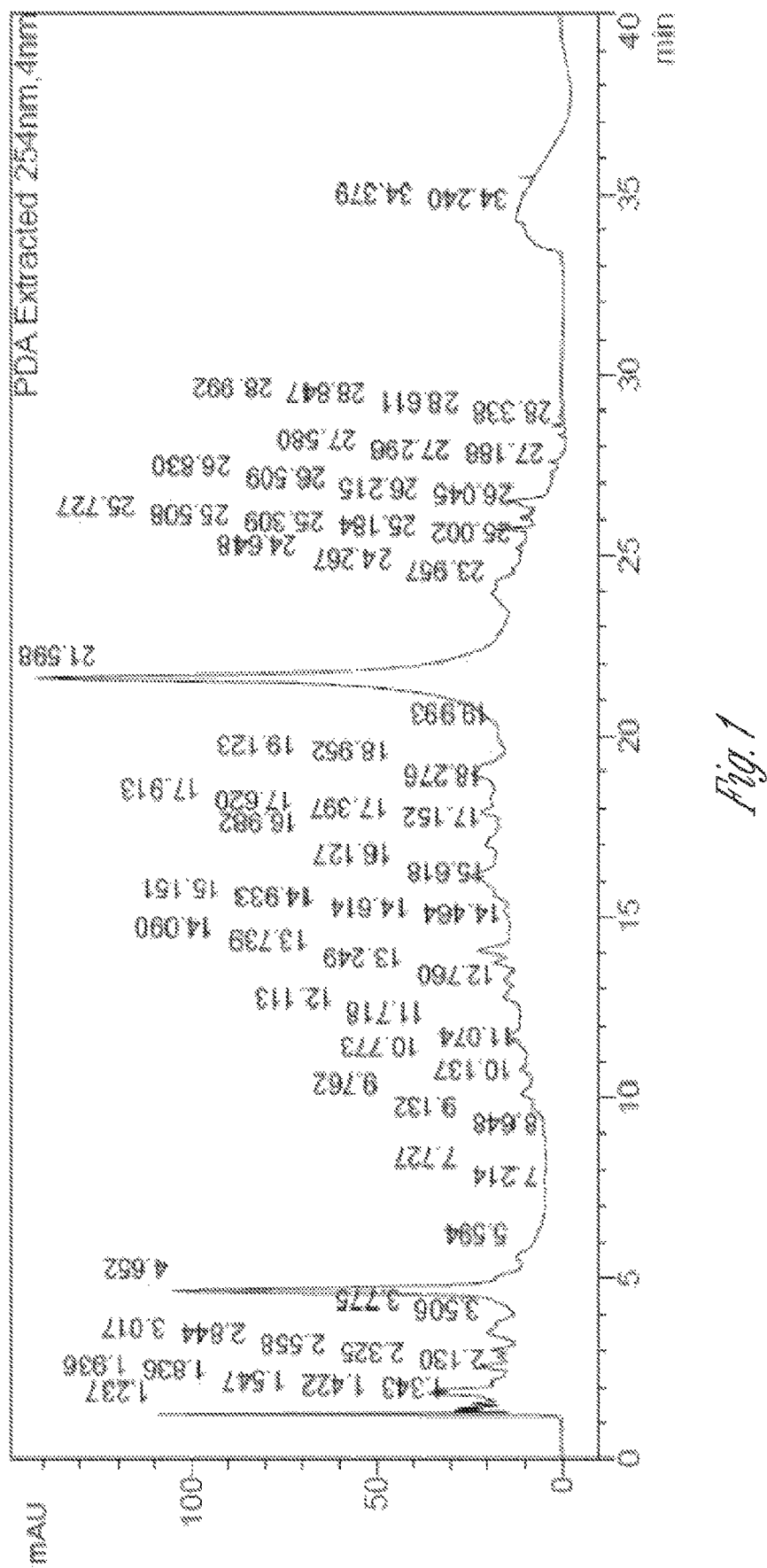
FIG. 1. Chromatogram of pomegranate seed extract with aqueous base at 254 nm.

Solid-phase extraction (SPE) is a separation process by which compounds that are dissolved or suspended in a liquid mixture are separated from other compounds in the mixture according to their physical and chemical properties. Analytical laboratories use SPE to concentrate and purify samples for analysis. SPE uses the affinity of solutes dissolved or suspended in a liquid (known as the mobile phase) for a solid through which the sample is passed (known as the stationary phase) to separate a mixture into desired and undesired components. The result is that either the desired analytes of interest or undesired impurities in the sample are retained on the stationary phase. The portion that passes through the stationary phase is collected or discarded, depending on whether it contains the desired analytes or undesired impurities. If the portion retained on the stationary phase includes the desired analytes, they can then be removed from the stationary phase for collection in an additional step, in which the stationary phase is rinsed with an appropriate eluent. The stationary phase comes in the form of, for example, a packed syringe-shaped cartridge, a 96 well plate, a 47- or 90-mm flat disk, or a MEPS device, each of which can be mounted on its specific type of extraction manifold. The manifold allows multiple samples to be processed by holding several SPE media in place and allowing for an equal number of samples to pass through them simultaneously. A typical cartridge SPE manifold can accommodate up to 24 cartridges, while a typical disk SPE manifold can accommodate 6 disks. Most SPE manifolds are equipped with a vacuum port. Application of vacuum speeds up the extraction process by pulling the liquid sample through the stationary phase. The analytes are collected in sample tubes inside or below the manifold after they pass through the stationary phase. Solid phase extraction cartridges and disks are available with a variety of stationary phases, each of which can separate analytes according to different chemical properties. Most stationary phases are based on silica that has been bonded to a specific functional group. Some of these functional groups include hydrocarbon chains of variable length (for reversed phase SPE), quaternary ammonium or amino groups (for anion exchange), and sulfonic acid or carboxyl groups (for cation exchange).

Normal Phase SPE Procedure

A typical solid phase extraction involves four basic steps. First, the cartridge is equilibrated with a non-polar solvent or slightly polar, which wets the surface and penetrates the bonded phase. Then water, or buffer of the same composition as the sample, is typically washed through the column to wet the silica surface. The sample is then added to the cartridge. As the sample passes through the stationary phase, the analytes in the sample will interact and retain on the sorbent while the solvent, salts, and other impurities pass through the cartridge. After the sample is loaded, the cartridge is washed with buffer or solvent to remove further impurities. Then, the analyte is eluted with a non-polar solvent or a buffer of the appropriate pH.

Reversed Phase SPE

Reversed phase SPE separates analytes based on their polarity. The stationary phase of a reversed phase SPE cartridge is derivatized with hydrocarbon chains, which retain compounds of mid to low polarity due to the hydrophobic effect. The analyte can be eluted by washing the cartridge with a non-polar solvent, which disrupts the interaction of the analyte and the stationary phase.

Ion Exchange SPE

Ion exchange sorbents separate analytes based on electrostatic interactions between the analyte of interest and the charged groups on the stationary phase. For ion exchange to occur, both the stationary phase and sample must be at a pH where ion-ion interactions may occur.

Anion Exchange

Anion exchange sorbents are derivatized with positively charged functional groups that interact and retain negatively charged anions, such as deprotonated acids. Strong anion exchange sorbents contain quaternary ammonium groups that have a permanent positive charge in aqueous solutions, and weak anion exchange sorbents use amine groups which are charged when the pH is below about 9. Strong anion exchange sorbents are useful because any strongly acidic impurities in the sample will bind to the sorbent and usually will not be eluted with the analyte of interest; to recover a strong acid a weak anion exchange cartridge should be used. To elute the analyte from either the strong or weak sorbent, the stationary phase is washed with a solvent that neutralizes the charge of either the analyte, the stationary phase, or both. Once the charge is neutralized, the electrostatic interaction between the analyte and the stationary phase no longer exists and the analyte will elute from the cartridge.

Cation Exchange

Cation exchange sorbents are derivatized with functional groups that interact and retain positively charged cations, such as protonated amines. Strong cation exchange sorbents contain aliphatic sulfonic acid groups that are always negatively charged in aqueous solution, and weak cation exchange sorbents contain aliphatic carboxylic acids, which are charged when the pH is above about 5. Strong cation exchange sorbents are useful because any strongly basic impurities in the sample will bind to the sorbent and usually will not be eluted with the analyte of interest; to recover a strong base a weak cation exchange cartridge should be used. To elute the analyte from either the strong or weak sorbent, the stationary phase is washed with a solvent that neutralizes ionic interaction between the analyte and the stationary phase.

HPLC

High-performance liquid chromatography (sometimes referred to as high-pressure liquid chromatography), HPLC, is a chromatographic technique used to separate a mixture of compounds in analytical chemistry and biochemistry with the purpose of identifying, quantifying and purifying the individual components of the mixture. Some common examples are the separation and quantitation of performance enhancement drugs (e.g. steroids) in urine samples, or of vitamin D levels in serum. HPLC typically utilizes different types of stationary phases (i.e. sorbents) contained in columns, a pump that moves the mobile phase and sample components through the column, and a detector capable of providing characteristic retention times for the sample components and area counts reflecting the amount of each analyte passing through the detector. The detector may also provide additional information related to the analyte, (e.g., UV/Vis spectroscopic data, if so equipped). Analyte retention time varies depending on the strength of its interactions with the stationary phase, the composition and flow rate of mobile phase used, and on the column dimensions. HPLC is a form of liquid chromatography that utilizes small size columns (typically 250 mm or shorter and 4.6 mm i.d. or smaller; packed with smaller particles), and higher mobile phase pressures compared to ordinary liquid chromatography. With HPLC, a pump (rather than gravity) provides the higher pressure required to move the mobile phase and sample components through the densely packed column. The increased density arises from the use of smaller sorbent particles. Such particles are capable of providing better separation on columns of shorter length when compared to ordinary column chromatography.

The sample to be separated and analyzed is introduced, in a discrete small volume, into the stream of mobile phase percolating through the column. The components of the sample move through the column at different velocities, which are functions of specific physical or chemical interactions with the stationary phase. The velocity of each component depends on its chemical nature, on the nature of the stationary phase (column) and on the composition of the mobile phase. The time at which a specific analyte elutes (emerges from the column) is called the retention time. The retention time measured under particular conditions is considered an identifying characteristic of a given analyte. The use of smaller particle size packing materials require the use of higher operational pressure ("backpressure") and typically improves chromatographic resolution (i.e. the degree of separation between consecutive analytes emerging from the column). Common mobile phases used include any miscible combination of water with various organic solvents (the most common are acetonitrile and methanol). Some HPLC techniques use water free mobile phases (see Normal Phase HPLC below). The aqueous component of the mobile phase may contain buffers, acids (such as formic, phosphoric or trifluoroacetic acid) or salts to assist in the separation of the sample components. The composition of the mobile phase may be kept constant ("isocratic elution mode") or varied ("gradient elution mode") during the chromatographic analysis. Isocratic elution is typically effective in the separation of sample components that are not very dissimilar in their affinity for the stationary phase.

In gradient elution the composition of the mobile phase is varied typically from low to high eluting strength. The eluting strength of the mobile phase is reflected by analyte retention times with high eluting strength producing fast elution (=short retention times). A typical gradient profile in reversed phase chromatography might start at 5% acetonitrile (in water or aqueous buffer) and progress linearly to 95% acetonitrile over 5-25 minutes. Period of constant mobile phase composition may be part of any gradient profile. For example, the mobile phase composition may be kept constant at 5% acetonitrile for 1-3 minutes, followed by a linear change up to 95% acetonitrile.

The composition of the mobile phase depends on the intensity of interactions between analytes and stationary phase (e.g. hydrophobic interactions in reversed-phase HPLC). Depending on their affinity for the stationary and mobile phases analytes partition between the two during the separation process taking place in the column. This partitioning process is similar to that which occurs during a liquid-liquid extraction but is continuous, not step-wise. In this example, using a water/acetonitrile gradient, more hydrophobic components will elute (come off the column) late, once the mobile phase gets more concentrated in acetonitrile (i.e. in a mobile phase of higher eluting strength).

The choice of mobile phase components, additives (such as salts or acids) and gradient conditions depend on the nature of the column and sample components. Often a series of trial runs are performed with the sample in order to find the HPLC method that gives the best separation.

Partition Chromatography

The partition coefficient principle has been applied in paper chromatography, thin layer chromatography, gas phase and liquid-liquid applications. Partition chromatography uses a retained solvent, on the surface or within the grains or fibers of an "inert" solid supporting matrix as with paper chromatography; or takes advantage of some coulombic and/or hydrogen donor interaction with the solid support. Molecules equilibrate (partition) between a liquid stationary phase and the eluent. Known as Hydrophilic Interaction Chromatography (HILIC) in HPLC, this method separates analytes based on polar differences. HILIC most often uses a bonded polar stationary phase and water miscible, high organic concentration, mobile phases. Partition HPLC has been used historically on unbonded silica or alumina supports. Each works effectively for separating analytes by relative polar differences. HILIC bonded phases have the advantage of separating acidic, basic and neutral solutes in a single chromatogram.

The polar analytes diffuse into a stationary water layer associated with the polar stationary phase and are thus retained. Retention strengths increase with increased analyte polarity, and the interaction between the polar analyte and the polar stationary phase (relative to the mobile phase) increases the elution time. The interaction strength depends on the functional groups in the analyte molecule which promote partitioning but can also include coulombic (electrostatic) interaction and hydrogen donor capability.

Use of more polar solvents in the mobile phase will decrease the retention time of the analytes, whereas more hydrophobic solvents tend to increase retention times.

Normal-Phase Chromatography

Normal-phase HPLC (NP-HPLC), or adsorption chromatography, separates analytes based on their affinity for a polar stationary surface such as silica, hence it is based on analyte ability to engage in polar interactions (such as hydrogen-bonding or dipole-dipole type of interactions) with the sorbent surface. NP-HPLC uses a non-polar, non-aqueous mobile phase, and works effectively for separating analytes readily soluble in non-polar solvents. The analyte associates with and is retained by the polar stationary phase. Adsorption strengths increase with increased analyte polarity. The interaction strength depends not only on the functional groups present in the structure of the analyte molecule, but also on steric factors. The effect of steric hindrance on interaction strength allows this method to resolve (separate) structural isomers.

The use of more polar solvents in the mobile phase will decrease the retention time of analytes, whereas more hydrophobic solvents tend to induce slower elution (increased retention times). Very polar solvents such as traces of water in the mobile phase tend to adsorb to the solid surface of the stationary phase forming a stationary bound (water) layer which is considered to play an active role in retention. This behavior is somewhat peculiar to normal phase chromatography because it is governed almost exclusively by an adsorptive mechanism (i.e., analytes interact with a solid surface rather than with the solvated layer of a ligand attached to the sorbent surface; see also reversed-phase HPLC below). Adsorption chromatography is still widely used for structural isomer separations in both column and thin-layer chromatography formats on activated (dried) silica or alumina supports.

Displacement Chromatography

The basic principle of displacement chromatography is: A molecule with a high affinity for the chromatography matrix (the displacer) will compete effectively for binding sites, and thus displace all molecules with lesser affinities. There are distinct differences between displacement and elution chromatography. In elution mode, substances typically emerge from a column in narrow, Gaussian peaks. Wide separation of peaks, e.g., to baseline, is desired in order to achieve maximum purification. The speed at which any component of a mixture travels down the column in elution mode depends on many factors. But for two substances to travel at different speeds, and thereby be resolved, there must be substantial differences in some interaction between the biomolecules and the chromatography matrix. Operating parameters are adjusted to maximize the effect of this difference. In many cases, baseline separation of the peaks can be achieved only with gradient elution and low column loadings. Thus, two drawbacks to elution mode chromatography, especially at the preparative scale, are operational complexity, due to gradient solvent pumping, and low throughput, due to low column loadings. Displacement chromatography has advantages over elution chromatography in that components are resolved into consecutive zones of pure substances rather than "peaks". Because the process takes advantage of the nonlinearity of the isotherms, a larger column feed can be separated on a given column with the purified components recovered at significantly higher concentrations.

Reversed-Phase Chromatography (RPC)

Reversed phase HPLC (RP-HPLC) has a non-polar stationary phase and an aqueous, moderately polar mobile phase. One common stationary phase is a silica which has been surface-modified with $RMe_2SiCl$, where R is a straight chain alkyl group such as $C_{18}H_{37}$ or $C_8H_{17}$. With such stationary phases, retention time is longer for molecules that are less polar, while polar molecules elute more readily (early in the analysis). An investigator can increase retention times by adding more water to the mobile phase; thereby making the affinity of the hydrophobic analyte for the hydrophobic stationary phase stronger relative to the now more hydrophilic mobile phase. Similarly, an investigator can decrease retention time by adding more organic solvent to the eluent. RP-HPLC is so commonly used that it is often incorrectly referred to as "HPLC" without further specification. The pharmaceutical industry regularly employs RP-HPLC to qualify drugs before their release.

RP-HPLC operates on the principle of hydrophobic interactions, which originate from the high symmetry in the dipolar water structure and play the most important role in all processes in life science. RP-HPLC allows the measurement of these interactive forces. The binding of the analyte to the stationary phase is proportional to the contact surface area around the non-polar segment of the analyte molecule upon association with the ligand on the stationary phase. This solvophobic effect is dominated by the force of water for "cavity-reduction" around the analyte and the $C_{18}$-chain versus the complex of both. The energy released in this process is proportional to the surface tension of the eluent (water: $7.3 \times 10^{-6}$ $J/cm^2$, methanol: $2.2 \times 10^{-6}$ $J/cm^2$) and to the hydrophobic surface of the analyte and the ligand respectively. The retention can be decreased by adding a less polar solvent (methanol, acetonitrile) into the mobile phase to reduce the surface tension of water. Gradient elution uses this effect by automatically reducing the polarity and the surface tension of the aqueous mobile phase during the course of the analysis.

Structural properties of the analyte molecule play an important role in its retention characteristics. In general, an analyte with a larger hydrophobic surface area (C—H, C—C, and generally non-polar bonds, such as S—S and others) is retained longer because it is non-interacting with the water structure. On the other hand, analytes with higher polar surface area (conferred by the presence of polar groups, such as —OH, —$NH_2$, COO— or —$NH_3$+ in their structure)are less retained as they are better integrated into water. Such interactions are subject to steric effects in that very large molecules may have only restricted access to the pores of the stationary phase, where the interactions with surface ligands (alkyl chains) take place. Such surface hindrance typically results in less retention.

Retention time increases with hydrophobic (non-polar) surface area. Branched chain compounds elute more rapidly than their corresponding linear isomers because the overall surface area is decreased. Similarly organic compounds with single C—C-bonds elute later than those with a C=C or C—C-triple bond, as the double or triple bond is shorter than a single C—C-bond.

Aside from mobile phase surface tension (organizational strength in eluent structure), other mobile phase modifiers can affect analyte retention. For example, the addition of inorganic salts causes a moderate linear increase in the surface tension of aqueous solutions (ca. $1.5 \times 10^{-7}$ $J/cm^2$ per Mol for NaCl, $2.5 \times 10^{-7}$ $J/cm^2$ per Mol for $(NH_4)_2SO_4$), and because the entropy of the analyte-solvent interface is controlled by surface tension, the addition of salts tend to increase the retention time. This technique is used for mild separation and recovery of proteins and protection of their biological activity in protein analysis (hydrophobic interaction chromatography, HIC).

Another important factor is the mobile phase pH since it can change the hydrophobic character of the analyte. For this reason most methods use a buffering agent, such as sodium phosphate, to control the pH. Buffers serve multiple purposes: control of pH, neutralize the charge on the silica surface of the stationary phase and act as ion pairing agents to neutralize analyte charge. Ammonium formate is commonly added in mass spectrometry to improve detection of certain analytes by the formation of analyte-ammonium adducts. A volatile organic acid such as acetic acid, or most commonly formic acid, is often added to the mobile phase if mass spectrometry is used to analyze the column effluent. Trifluoroacetic acid is used infrequently in mass spectrometry applications due to its persistence in the detector and solvent delivery system, but can be effective in improving retention of analytes such as carboxylic acids in applications utilizing other detectors, as it is a fairly strong organic acid. The effects of acids and buffers vary by application but generally improve chromatographic resolution.

Size-Exclusion Chromatography

Size-exclusion chromatography (SEC), also known as gel permeation chromatography or gel filtration chromatography, separates particles on the basis of size. It is generally a low-resolution chromatography and thus it is often reserved for the final, "polishing" step of a purification. It is also useful for determining the tertiary structure and quaternary structure of purified proteins. SEC is used primarily for the analysis of large molecules such as proteins or polymers. SEC works by trapping these smaller molecules in the pores of a particle. The larger molecules simply pass by the pores as they are too large to enter the pores. Larger molecules therefore flow through the column quicker than smaller molecules, that is, the smaller the molecule, the longer the retention time.

This technique is widely used for the molecular weight determination of polysaccharides. SEC is the official technique (suggested by European pharmacopeia) for the molecular weight comparison of different commercially available low-molecular weight heparins.

Ion-Exchange Chromatography

In ion-exchange chromatography (IC), retention is based on the attraction between solute ions and charged sites bound to the stationary phase. Ions of the same charge are excluded. Types of ion exchangers include: polystyrene resins which allow cross linkage which increases the stability of the chain. Higher cross linkage reduces resin swelling, which increases the equilibration time and ultimately improves selectivity; cellulose and dextran ion exchangers (gels) which possess larger pore sizes and low charge densities making them suitable for protein separation; and controlled-pore glass or porous silica. In general, ion exchangers favor the binding of ions of higher charge and smaller radius.

An increase in counter ion (with respect to the functional groups in resins) concentration reduces the retention time. A decrease in pH reduces the retention time in cation exchange while an increase in pH reduces the retention time in anion exchange. By lowering the pH of the solvent in a cation exchange column, for instance, more hydrogen ions are available to compete for positions on the anionic stationary phase, thereby eluting weakly bound cations.

This form of chromatography is widely used in the following applications: water purification, preconcentration of trace components, ligand-exchange chromatography, ion-exchange chromatography of proteins, high-pH anion-exchange chromatography of carbohydrates and oligosaccharides, and others.

Bioaffinity Chromatography

This chromatographic process relies on the property of biologically active substances to form stable, specific, and reversible complexes. The formation of these complexes involves the participation of common molecular forces such as the Van der Waals interaction, electrostatic interaction, dipole-dipole interaction, hydrophobic interaction, and the hydrogen bond. An efficient, biospecific bond is formed by a simultaneous and concerted action of several of these forces in the complementary binding sites.

Aqueous Normal-Phase Chromatography

Aqueous normal-phase chromatography (ANP) is a chromatographic technique which encompasses the mobile phase region between reversed-phase chromatography (RP) and organic normal phase chromatography (ONP). This technique is used to achieve unique selectivity for hydrophilic compounds, showing normal phase elution using reverse-phase solvents.

Isocratic Flow and Gradient Elution

A separation in which the mobile phase composition remains constant throughout the procedure is termed isocratic (meaning constant composition). The mobile phase composition does not have to remain constant. A separation in which the mobile phase composition is changed during the separation process is described as a gradient elution. One example is a gradient starting at 10% methanol and ending at 90% methanol after 20 minutes. The two components of the mobile phase are typically termed "A" and "B"; A is the "weak" solvent which allows the solute to elute only slowly, while B is the "strong" solvent which rapidly elutes the solutes from the column. In reverse-phase chromatography, solvent A is often water or an aqueous buffer, while B is an organic solvent miscible with water, such as acetonitrile, methanol, THF, or isopropanol.

In isocratic elution, peak width increases with retention time linearly according to the equation for N, the number of theoretical plates. This leads to the disadvantage that late-eluting peaks get very flat and broad. Their shape and width may keep them from being recognized as peaks.

Gradient elution decreases the retention of the later-eluting components so that they elute faster, giving narrower (and taller) peaks for most components. This also improves the peak shape for tailed peaks, as the increasing concentration of the organic eluent pushes the tailing part of a peak forward. This also increases the peak height (the peak looks "sharper"), which is important in trace analysis. The gradient program may include sudden "step" increases in the percentage of the organic component, or different slopes at different times—all according to the desire for optimum separation in minimum time.

In isocratic elution, the selectivity does not change if the column dimensions (length and inner diameter) change—that is, the peaks elute in the same order. In gradient elution, the elution order may change as the dimensions or flow rate change.

The driving force in reversed phase chromatography originates in the high order of the water structure. The role of the organic component of the mobile phase is to reduce this high order and thus reduce the retarding strength of the aqueous component.

Parameters

Internal Diameter

The internal diameter (ID) of an HPLC column is one parameter that influences the detection sensitivity and separation selectivity in gradient elution. It also determines the quantity of analyte that can be loaded onto the column. Larger columns are usually seen in industrial applications, such as the purification of a drug product for later use. Low-ID columns have improved sensitivity and lower solvent consumption at the expense of loading capacity. Larger ID columns (over 10 mm) are used to purify usable amounts of material because of their large loading capacity. Analytical scale columns (4.6 mm) have been the most common type of columns. They are used in traditional quantitative analysis of samples and often use a UV-Vis absorbance detector. Narrow-bore columns (1-2 mm) are used for applications when more sensitivity is desired either with special UV-Vis detectors, fluorescence detection or with other detection methods like liquid chromatography-mass spectrometry Capillary columns (under 0.3 mm) are used almost exclusively with alternative detection means such as mass spectrometry. They are usually made from fused silica capillaries, rather than the stainless steel tubing that larger columns employ.

Particle Size

Most traditional HPLC is performed with the stationary phase attached to the outside of small spherical silica particles (very small beads). These particles come in a variety of sizes with 5 µm beads being the most common. Smaller particles generally provide more surface area and better separations, but the pressure required for optimum linear velocity increases by the inverse of the particle diameter squared.

This means that changing to particles that are half as big, keeping the size of the column the same, will double the performance, but increase the required pressure by a factor of four. Larger particles are used in preparative HPLC (column diameters 5 cm up to >30 cm) and for non-HPLC applications such as solid-phase extraction.

Pore Size

Many stationary phases are porous to provide greater surface area. Small pores provide greater surface area while larger pore size has better kinetics, especially for larger analytes. For example, a protein which is only slightly smaller than a pore might enter the pore but does not easily leave once inside.

Pump Pressure

Pumps vary in pressure capacity, but their performance is measured on their ability to yield a consistent and reproducible flow rate. Pressure may reach as high as 40 MPa (6000 lbf/in$^2$), or about 400 atmospheres. Modern HPLC systems have been improved to work at much higher pressures, and therefore are able to use much smaller particle sizes in the columns (<2 μm). These "Ultra High Performance Liquid Chromatography" systems or RSLC/UHPLCs can work at up to 100 MPa (15,000 lbf/in$^2$), or about 1000 atmospheres. The term "UPLC" is a trademark of the Waters Corporation, but is sometimes used to refer to the more general technique.

In chromatography, the simulated moving bed (SMB) technique is a variant of high performance liquid chromatography; it is used to separate particles and/or chemical compounds that would be difficult or impossible to resolve otherwise. This increased separation is brought about by a valve-and-column arrangement that is used to lengthen the stationary phase indefinitely.

In the moving bed technique of preparative chromatography the feed entry and the analyte recovery are simultaneous and continuous, but because of practical difficulties with a continuously moving bed in the simulated moving bed technique instead of moving the bed, the sample inlet and the analyte exit positions are moved continuously, giving the impression of a moving bed.

True moving bed chromatography (MBC) is only a theoretical concept. Its simulation, SMBC is achieved by the use of a multiplicity of columns in series and a complex valve arrangement, which provides for sample and solvent feed, and also analyte and waste takeoff at appropriate locations of any column, whereby it allows switching at regular intervals the sample entry in one direction, the solvent entry in the opposite direction, whilst changing the analyte and waste takeoff positions appropriately as well.

One advantage of the SMBC is high speed, because a system could be near continuous, whilst its disadvantage is that it only separates binary mixtures. It does not say, but perhaps it can be assumed that this is equivalent with the separation of a single component from a group of compounds. With regard to efficiency it compares with simple chromatography technique like continuous distillation does with batch distillation.

Specifically, an SMB system has two or more identical columns, which are connected to the mobile phase pump, and each other, by a multi-port valve. The plumbing is configured in such a way that:

a) all columns will be connected in series, regardless of the valve's position;
b) each different position of the valve will reconnect the columns to one another in one possible sequential arrangement of the columns; and
c) all possible positions of the valve will arrange the columns in every possible sequential order.

For example, consider a case where two HPLC columns, A and B, are connected to one another, and the mobile-phase pump, via a six-port, two-position valve (e.g., a Rheodyne 7000). One valve position will distribute the flow in the manner Pump→Column A→Column B→Waste, while the other position will distribute the flow in the manner Pump→Column B→Column A→Waste.

Consequently, switching of the valve will "leapfrog" the columns over one another. If elution across two columns in series is not adequate to resolve two compounds in a given run, the eluent can then be made to go through 3, 4, 5 . . . columns in additional runs by carefully timed switching. This increases the number of theoretical plates until separation can be attained.

When affinity differences between molecules are very small, it is sometimes not possible to improve resolution via mobile- or stationary-phase changes. In these cases, the multi-pass approach of SMB can separate mixtures of those compounds by allowing their small retention time differences to accumulate.

At industrial scale an SMB chromatographic separator is operated continuously, requiring less resin and less solvent than batch chromatography. The continuous operation facilitates operation control and integration into production plants.

In size exclusion chromatography, where the separation process is driven by entropy, it is not possible to increase the resolution attained by a column via temperature or solvent gradients. Consequently, these separations often require SMB, to create usable retention time differences between the molecules or particles being resolved. SMB is also very useful in the pharmaceutical industry, where resolution of molecules having different chirality must be done on a very large scale.

Exemplary Compositions and Methods of Use

In one embodiment, the methods are employed to isolate skin whitening compounds in fruit or vegetable seed extracts, compounds including ellagic acid, or derivatives thereof or ellagitannins, or other compounds with anti-tyrosinase activity or skin whitening activity. A composition may comprise a skin whitening or tyrosinase inhibiting compound in an amount of about 1 μg to about 2000 mg of the compound per dose for a mammal weighing about 20 to 25 g. In one embodiment, the composition comprises a compound of the invention in an amount of about 1 mg to about 1000 mg, e.g., about 10 mg to about 100 mg, or an amount of about 0.1 μg to about 1000 μg, e.g., about 1 μg to about 10 μg. In one embodiment, the composition comprises a compound of the invention an amount of about 20 μg/kg to about 2000 μg/kg, e.g., about 50 μg/kg to about 500 μg/kg or about 100 μg/kg to about 400 μg/kg. Other anti-tyrosinase compounds or other skin whitening agents may be included. In addition to the active agent(s), one or more suitable pharmaceutically acceptable carriers may be used. As used herein, the term "pharmaceutically acceptable carrier" refers to an acceptable vehicle for administering a composition to mammals comprising one or more non-toxic excipients that do not react with or reduce the effectiveness of the pharmacologically active agents contained therein. The proportion and type of pharmaceutically acceptable carrier in the composition may vary, depending on the chosen route of administration. Suitable pharmaceutically acceptable carriers for the compositions of the present disclosure are described in the standard pharmaceutical texts. See, e.g., "Remington's Pharmaceutical Sciences", 18$^{th}$ Ed., Mack Publishing Company, Easton, Pa. (1990). Specific non-limiting examples of suitable pharmaceutically acceptable carriers include water, saline, dextrose, glycerol, ethanol, or the like and combinations thereof. Optionally, the composition may further comprise minor amounts of auxiliary substances such as antimicrobial agents, stabilizers, preservatives, and the like. Examples of suitable stabilizers include sugars such as sucrose and glycerol, encapsulating polymers, chelating agents such as ethylenediaminetetracetic acid (EDTA), proteins and polypeptides such as gelatin and polyglycine and combinations thereof.

Ellagic acid and its derivatives include compounds of formula (I):

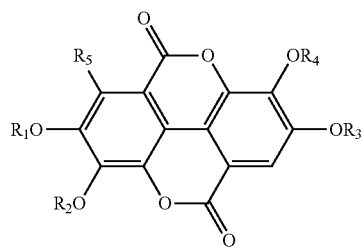

in which R1 to R4 are each, independently, hydrogen atoms, an alkyl group having 1 to 20 carbon atoms (e.g., 1 to 10 carbon atoms, or 1-6 carbon atoms), an alkoxy group having 1 to 20 carbon atoms (e.g., 1 to carbon atoms, or 1-6 carbon atoms), an alkoxy group having 1 to 20 carbon atoms (e.g., 1 to 10 carbon atoms, or y 1-6 carbon atoms), a poly(ethylene oxide) or poly(propylene oxide) or poly(ethylene/propylene oxide) (a copolymer of ethylene oxide and propylene oxide units) radical or a sugar radical, and R5 is a hydrogen atom, a hydroxyl group or an alkoxy group having 1 to 18 carbon atoms (e.g., 1 to 10 carbon atoms, or y 1-6 carbon atoms). These compounds are described in the patent U.S. Pat. No. 5,073,545, which is hereby incorporated by reference.

Exemplary Pharmaceutical Formulations

The therapeutic compositions described herein will typically include a carrier (e.g., solvent) and one or more active agents ("actives"), as described above. The compositions can be combined with other ingredients to provide pharmaceutical formulations. Pharmaceutical formulations will typically include the therapeutic composition, a pharmaceutically acceptable carrier, and optionally one or more additional ingredients that, for example, aid the formation of the desired delivery vehicle of the active. For topical administration, it will generally be desirable to administer the active agent to the skin as a composition or formulation, for example, in combination with a dermatologically acceptable carrier, where the composition or formulation may be a semi-solid, oil, or a liquid.

Thus, a topical composition typically includes an active and a pharmaceutically acceptable carrier for topical administration. The administration can be the topical application of a gel, a serum, a jelly, a cream, a lotion, a wax, an ointment, a solution, a paste, an aerosol, a patch, and/or a combination thereof Salts. In cases where actives are sufficiently basic or acidic to form stable nontoxic acid or base salts, administration of the actives as salts may be appropriate. Examples of pharmaceutically acceptable salts are organic acid addition salts formed with acids which form a physiological acceptable anion, for example, tosylate, methanesulfonate, acetate, propionate, citrate, malonate, tartrate, succinate, benzoate, ascorbate, α-ketoglutarate, and α-glycerophosphate. Pharmaceutically acceptable salts can also be mineral acid salts such as hydrochlorides, hydrobromides, and the like. Suitable salts may also be formed as halides, nitrates, phosphates, sulfates, bicarbonates, carbonate salts, and the like.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

Carriers. Active agents can be combined with a pharmaceutically acceptable carrier or diluent (e.g., a solvent) to produce a pharmaceutical composition or formulation. In such pharmaceutical formulations, the active agents or therapeutic composition can be combined with a "carrier" that is physiologically compatible with the skin of a human or animal to which it is topically administered. Typically the carrier is substantially inactive, with the exception of its intrinsic surfactant properties which may aid in the production of a solution or suspension of the active ingredients. The compositions may include other physiologically active constituents that do not interfere with the efficacy of the active agents in the composition. In some embodiments, the carriers can be liquid or gel-based materials for use in liquid or gel formulations. The specific formulations depend, in part, upon the desired routes or modes of administration.

Suitable carrier materials include any carrier or vehicle commonly used as a base for solutions, dispersions, emulsions, gels, creams, ointment, lotions, pastes, or foams, for topical administration.

Many suitable liquid or gel-based carriers are well-known in the art. The carrier should be able to dissolve or disperse an active at an effective level. Examples include water, physiological salt solutions, alcohols (e.g., methanol, ethanol, propanol, or butanol), glycerol, glycols (e.g., ethylene glycol, propylene glycol, or ethoxy diglycol), polyethylene glycol (e.g., MW 400 to 20,000), water-alcohol/glycol blends, and the like. Suitable carriers and diluents for certain embodiments include, for example, water, saline, isotonic saline solutions, for example, phosphate-buffered saline, aqueous dextrose, glycerol, ethoxy diglycol, dimethyl sulfoxide (DMSO), and the like, or combinations thereof.

Suitable carriers further include aqueous and oleaginous carriers such as, for example, white petrolatum, isopropyl myristate, lanolin or lanolin alcohols, mineral oil, fragrant or essential oil, nasturtium extract oil, sorbitan mono-oleate, cetostearyl alcohol (together or in various combinations), and detergents (e.g., polysorbates (Tweens) such as polysorbate 20, 40, 60, or 80; polyoxyl stearate; or sodium lauryl sulfate). One or more carrier materials can be mixed with water to form a lotion, gel, cream, semi-solid composition, or the like. Other suitable carriers include water-in-oil or oil-in-water emulsions and mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether, water, or combinations thereof. For example, emulsions containing water, glycerol stearate, glycerin, mineral oil, synthetic spermaceti, cetyl alcohol, or combinations thereof, may be used. Preservatives may also be included in the carrier, such as one or more of butylparaben, methylparaben, propylparaben, benzyl alcohol, and ethylene diamine tetraacetate salts. The composition of the carrier can be varied so long as it does not interfere significantly with the pharmacological activity of the active ingredients of the therapeutic composition.

Gelling Agents and Thickening Agents. The compositions described herein can include one or more gelling agents to increase the viscosity of the composition. Examples of gelling agents and thickening agents, include, but are not limited to, fatty acids, fatty acid salts and esters, fatty alcohols, synthetic polymers, modified celluloses, xanthan gum, or combinations thereof. Examples of suitable synthetic polymers include polyethylene glycol (PEG), polyvinylpyrrolidone (PVP), polyvinyl alcohol (PVA), various Pluronics (poloxamers), or carbomers (e.g., Carbomer 940 or Carbomer 934). Examples of suitable modified celluloses include methylcellulose, carboxymethylcellulose (CMC), hydroxyethylcellulose (HEC), hydroxymethyl cellulose (HMC), hydroxypropyl cellulose (HPC), hydroxypropylmethylcellulose (HPMC), or other cellulose-based gelling agents.

A variety of gelling agents is commercially available and can be obtained in many suitable molecular weights and ranges. Examples of thickening agents include lanolin, hard paraffin, liquid paraffin, white petrolatum, soft yellow paraffin or soft white paraffin, white beeswax, yellow beeswax, propolis (propoleum), cetostearyl alcohol, cetyl alcohol, dimethicones, emulsifying waxes, microcrystalline wax, oleyl alcohol and stearyl alcohol.

One or more gelling agents or thickening agents may be included in a single formulation. Such agents can be employed with liquid carriers to form spreadable gels, pastes, ointments, soaps, and the like, for application directly to the skin of the user.

Solutions and Dispersions. Solutions of an active or its salts can be prepared in water, optionally mixed with a nontoxic surfactant. Dispersions can be prepared in glycerol, liquid polyethylene glycols, triacetin, or in a pharmaceutically acceptable oil, or mixtures thereof. Under ordinary conditions of storage and use, preparations may contain a preservative to prevent the growth of microorganisms.

Pharmaceutical dosage forms can include sterile aqueous solutions or dispersions comprising the active ingredient adapted for the extemporaneous preparation of sterile solutions or dispersions, optionally encapsulated in liposomes. The ultimate dosage form should be fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, emu oil, nontoxic glyceryl esters, and suitable mixtures thereof. The proper fluidity of the composition can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the compositions can be brought about by agents delaying absorption, for example, aluminum monostearate and/or gelatin.

Solutions can be prepared by incorporating the active in a desired amount in the appropriate solvent or oil with various other ingredients enumerated herein, as desired, followed by optional filter sterilization. For powders used in the preparation of solutions, methods of preparation can include vacuum drying and freeze drying techniques, which yield a powder of the active plus any additional desired ingredient present in the prepared solutions.

Gels. Gels are clear, sticky, jelly-like semisolids or solids prepared from high molecular weight polymers in an aqueous or alcoholic base. Alcoholic gels are often drying and cooling. Non-alcoholic gels are more lubricating. Gels or jellies can be produced using a suitable gelling agent including, but not limited to, gelatin, tragacanth, a carbomer, or a cellulose derivative and may include glycerol as a humectant, an emollient, and/or a preservative. In some embodiments, gel formulations will include the same or similar ingredients as a solution or dispersion, with the addition of a gelling agent.

The gel can include a nonionic copolymer gelling agent. In one embodiment, the gelling agent is a nonionic polyoxyethylene-polyoxypropylene copolymer gel, for example, a Pluronic gel such as Pluronic F-127 (BASF Corp.), to provide a pluronic gel-based formulation. This gel can be advantageous because it is a liquid at low temperatures but rapidly sets at physiological temperatures, which confines the release of the agent to the site of application or immediately adjacent that site. Other formulations can be carboxymethylcellulose (CMC)-based formulations, hydroxymethyl cellulose (HMC)-based formulations, hydroxypropyl cellulose (HPC)-based formulations, or hydroxypropylmethylcellulose (HPMC)-based formulations, and the like.

Creams. Creams are viscous liquids or semisolid emulsions, either oil-in-water or water-in-oil. Cream bases are water-washable, and comprise an oil phase, an emulsifier, and an aqueous-phase. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant (a substance, such as glycerin, sorbitol, or urea, that absorbs or helps another substance retain moisture).

The emulsifier in a cream formulation is generally a nonionic, anionic, cationic, or amphoteric surfactant. Examples of emulsifiers include, but are not limited to, fatty alcohol polyoxyethylene ether (Peregal A-20), stearates such as polyoxylstearate (Softener SG), glyceryl stearate and pegylated forms of glyceryl stearate such as PEG-5 glyceryl stearate, cetyl alcohol, dithranol, or a combination thereof.

Oil-phase ingredients can include, but are not limited to, dimethicone, dimethiconol, cyclomethicone, diisopropyl adipate, cetyl alcohol, stearyl alcohol, paraffin, petrolatum, almond oil, stearic acid, or a combination thereof. In particular aspects, aqueous ingredients can include, but are not limited to, purified water, glycerol (glycerin), propylene glycol, ethyl paraben, a humectant, or a combination thereof.

In some embodiments, the cream further comprises one or more film formers including but not limiting to polyglycerylmethacrylate, acrylates/$C_{10}$-$C_{30}$ alkyl acrylate cross-polymers; antioxidant including but not limiting to tocopheryl acetate; preservatives including but not limiting to phenoxyethanol, benzyl alcohol; other additives including but not limiting to dicaprylyl ether, disodium EDTA, sodium hydroxide, and lactic acid.

In one embodiment, the cream can include purified water, polyglycerylmethacrylate, propylene glycol, petrolatum, dicaprylyl ether, PEG-5 glyceryl stearate, glycerin, dimethicone, dimethiconol, cetyl alcohol, sweet almond oil, acrylates/$C_{10}$-$C_{30}$ alkyl acrylate cross-polymers, tocopheryl acetate, phenoxyethanol, benzyl alcohol, disodium EDT A, sodium hydroxide, lactic acid, or any combination thereof.

In another embodiment, the cream can include glycerol, light liquid paraffin, soft white paraffin, dimethicone, squalane, methyl hydroxybenzoate, dichlorobenzyl alcohol, or any combination thereof.

Ointments. Ointments are semisolid preparations that include the active incorporated into a fatty, waxy, or synthetic base. Ointments are typically based on petrolatum or other petroleum derivatives. The specific ointment base to be used, as will be appreciated by those skilled in the art, is one that will provide for suitable drug delivery and other desired characteristics such as emolliency or the like. As with other carriers or vehicles, an ointment base is typically inert, stable, non-irritating and non-sensitizing.

Ointment bases may be generally grouped in four classes: oleaginous bases; emulsifiable bases; emulsion bases; and water-soluble bases. Oleaginous ointment bases can include, for example, vegetable oils, fats obtained from animals, and semisolid hydrocarbons obtained from petroleum. Emulsifiable ointment bases, also known as absorbent ointment bases, contain little or no water and can include, for example, hydroxystearin sulfate, anhydrous lanolin, and hydrophilic petrolatum. Emulsion ointment bases are either water-in-oil (W/O) emulsions or oil-in-water O/W) emulsions, and the oil components can include, for example, cetyl alcohol, glyceryl monostearate, lanolin, and stearic acid. Water-soluble ointment bases can be prepared from polyethylene glycols of varying molecular weight.

Lotions. Lotions are liquid or semiliquid preparations in which solid particles, including the active agent(s), are present in a water or alcohol base. Lotions are usually suspensions of solids, and can include a liquid oily emulsion of the oil-in-water type. Lotions are often desirable formulations because of the ease of applying a more fluid composition. It is generally advantageous for the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Serums. In general, serums have a lower viscosity relative to lotions and gels, and is typified by its rapid absorption, ability to penetrate into the deeper layers of the skin, together with a non-greasy finish and intensive formula with a very high concentration of active substance(s).

Pastes. Pastes are semisolid dosage forms in which the active agent is suspended in a suitable base. Depending on the nature of the base, pastes are divided between fatty pastes or those made from a single-phase aqueous gel. The base in a fatty paste is generally petrolatum, hydrophilic petrolatum, or the like. The pastes made from single-phase aqueous gels generally incorporate carboxymethylcellulose or the like as a base.

Foams. Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Accordingly, the composition described herein may be formulated for any desired form of topical or transdermal administration, including slow or delayed release preparations. Formulations may include known antioxidants (e.g., vitamin E); buffering agents; lubricants (e.g., synthetic or natural beeswax); sunscreens (e.g., para-aminobenzoic acid); and cosmetic agents (e.g., coloring agents, fragrances, essential oils, moisturizers, or drying agents).

An auxiliary agent such as casein, gelatin, albumin, or sodium alginate may also be included in various formulations. Adjuvants such as fragrances and additional antimicrobial agents can be added to optimize the properties for a given use.

Thus, the present disclosure also provides for the use of compositions having ellagic acid, derivatives thereof, or ellagitannins, in a cosmetic preparation for depigmenting and/or whitening the human skin or the hair of the body or scalp. It further provides for the use of this composition for the manufacture of a preparation for depigmenting and/or whitening the human skin or the hair of the body or scalp, after applying to the skin or the hair of the body or scalp the composition. The composition may also include other skin whitening agents, e.g., kojic acid, arbutin, or hydroquinone.

The composition may be present in any of the pharmaceutical forms which are normally used for topical application, e.g., aqueous, aqueous-alcoholic or oily solutions, oil-in-water or water-in-oil or multiple emulsions, aqueous or oily gels, liquid, pastelike or solid anhydrous products, oil dispersed in an aqueous phase with the aid of spherules, it being possible for these spherules to be polymeric nanocapsules or more for example, lipid vesicles of ionic and/or nonionic type.

Moreover, it may be advantageous to dissolve the ellagic acid in a basic solution with a pH greater than 14, then to acidify this solution to a pH of between approximately 6 and 8 prior to its incorporation into the composition.

The present composition may be more or less fluid and may have the appearance of a white or colored cream, a pomade, a milk, a lotion, a serum, a paste or a mousse. The composition can also be applied in aerosol form to the skin or hair of the body or scalp. Additionally, the present composition can be present in solid form and, for example, in stick form. It may be used as a care product and/or as a makeup product for the skin. It may also be in the form of shampoo or conditioner.

Conventionally, the composition may also comprise one or more adjuvants which are customary in the cosmetic field, such as hydrophilic or lipophilic gelling agents, hydrophilic or lipophilic active principles, preservatives, antioxidants, solvents, fragrances, fillers, filters, pigments, odor absorbers and colorants. The amounts of these various adjuvants are those which are conventionally used in the field in question, and, for example, are from 0.01 to 20% of the total weight of the composition. These adjuvants, depending on their nature, may be introduced into the fatty phase, into the aqueous phase, into the lipid vesicles and/or into the nanoparticles. In any case, these adjuvants and their proportions will be selected so as not to detract from the desired properties of the combination of depigmenting agents according to the invention. Such adjuvant selection is well within the skill of one of ordinary skill in the art.

When the composition is an emulsion, the proportion of the fatty phase fro example ranges from 5 to 80% by weight, or from 5 to 50% by weight, relative to the total weight of the composition. The oils, emulsifiers and coemulsifiers used in the composition in emulsion form are selected from those which are conventionally used. The emulsifier and coemulsifier are present in the composition in a proportion ranging from 0.3 to 30% by weight, e.g., from 0.5 to 20% by weight, relative to the total weight of the composition.

Suitable oils which may be used include mineral oils (liquid petroleum), oils of vegetable origin (avocado oil, soya oil, sunflower oil, or cranberry oil), black cumin oil, raspberry oil, oils of animal origin (lanolin), synthetic oils (perhydrosqualene), silicone oils (cyclomethicone) and fluorinated oils (perfluoropolyethers). Fatty alcohols (cetyl alcohol), fatty acids, and waxes (camauba wax, ozokerite) may also be used as fatty substances.

Suitable emulsifiers and coemulsifiers which may be used include fatty acid polyethylene glycol esters such as PEG-20 stearate and fatty acid glycerol esters such as glyceryl stearate.

Suitable hydrophilic gelling agents which may be used include carboxyvinyl polymers (carbomer), acrylic copolymers such as acrylate/alkyl acrylate copolymers, polyacrylamides, polysaccharides, natural gums and clays, and, as lipophilic gelling agents, mention may be made of modified clays such as bentones, metal salts of fatty acids, hydrophobic silica and polyethylenes.

The depigmenting or lightening composition is applied in accordance with conventional regimens of depigmentation treatment.

EXEMPLARY EMBODIMENTS

In one embodiment, the disclosure provides a method to isolate compounds having anti-tyrosinase activity. The method includes providing a cold press processed fruit seed extract dissolved or suspended in water, a lower alcohol or a water-lower alcohol mix to provide a first mixture having solids and a liquid having compounds including ellagic acid or an ellagitannin; and separating the liquid from the solids to provide for a fraction that is enhanced in ellagic acid or ellagitannin and has anti-tyrosinase activity. In one embodiment, the method provides for isolatation of ellagic acid or ellagitannin. The method includes providing a raspberry, blackberry or blueberry seed extract suspended in water, a lower alcohol or a water-lower alcohol mix, thereby providing a mixture, incubating the mixture under conditions that allow for extraction of compounds including ellagic acid or ellagitannin; and separating the extracted compounds to provide for a fraction that is enhanced in ellagic acid or ellagitannin. In one embodiment, the lower alcohol is propanol, butanol, ethanol or methanol. In one embodiment, the water-lower alcohol mix comprises 70:30 methanol:water. In one embodiment, the fraction inhibits eumelanin or pheomelanin production in human skin. In one embodiment, the extract is a powder. In one embodiment, the method further comprises removing the solvent from the extracted compounds. In one embodiment, the separation comprises filtering the mixture. In one embodiment, the separation further includes subjecting the mixture to separation on a C8 column, to separation on a C18 solid phase extraction column or to separation on an ion exchange chromatography column, or any combination thereof. In one embodiment, the separation further includes subjecting the mixture to high pressure liquid chromatography.

In one embodiment, a topical composition comprising an extract of raspberry seed, blackberry seed, blueberry seed or pomegranate seed having ellagic acid or ellagitannin is provided. In one embodiment, the composition further comprises a solvent, e.g., an alcohol, oil or water. In one embodiment, the composition is a lotion, serum, cream, solid or gel. In one embodiment, the extract is a raspberry seed extract. In one embodiment, the composition has about 10 wt % to about 30 wt % of the extract. In one embodiment, the composition has about 10 wt % to about 90 wt % of the extract. In one embodiment, the composition has about 5 wt % to about 20 wt % of the extract. In one embodiment, the composition further comprises an emollient. In one embodiment, the emollient is about 5 wt % to about wt %, 10 wt % to about 30 wt %, 5 wt % to about 10 wt % or 1 wt % to about 5 wt % of the composition. In one embodiment, the composition further comprises a thickener. In one embodiment, the composition further comprises a preservative. In one embodiment, the thickener is about 0.05 wt % to about 2 wt %. In one embodiment, the composition further comprises one or more emulsifiers. In one embodiment, the emulsifier is about 1 wt % to about 5 wt % of the composition. In one embodiment, the composition further comprises a buffer.

In one embodiment, a topical liquid composition comprising an amount of an extract of raspberry seed, blackberry seed, blueberry seed or pomegranate seed having ellagic acid or ellagitannin effective to lighten human skin and a solvent is provided. In one embodiment, the extract is a raspberry seed extract. In one embodiment, the composition has about 10 wt % to about 30 wt %, about 5 wt % to about 20 wt %, or about 15 wt % to about 35 wt % of the extract. In one embodiment, the composition further comprises an emollient. In one embodiment, the emollient comprises about 10 wt % to about 30 wt %, about 5 wt % to about 20 wt %, or about 15 wt % to about 35 wt %. In one embodiment, the extract is a raspberry seed extract comprising about 10 wt % to about 30 wt and the solvent comprises ethanol.

In one embodiment, a topical serum composition comprising an amount of an extract of raspberry seed, blackberry seed, blueberry seed or pomegranate seed having ellagic acid or ellagitannin effective to lighten human skin and a solvent. In one embodiment, the extract is a raspberry seed extract. In one embodiment, the composition has about 10 wt % to about 30 wt %, 20 wt % to about 50 wt %, 50 wt % to about 90 wt %, or about 10 wt % to about 90 wt % of the extract. In one embodiment, the composition of further comprises an emollient. In one embodiment, the emollient comprises about 5 wt % to about 30 wt %, about 5 wt % to about 10 wt %, or about 15 wt % to about 35 wt % of the composition. In one embodiment, the extract is a raspberry seed extract comprising about 10 wt % to about 90 wt % and the solvent comprises oil. In one embodiment, the composition further comprises an emollient at about 5 wt % to about 20 wt %, 5 wt % to about 30 wt % or about 10 wt % to about 40 wt %. In one embodiment, the extract is a raspberry seed extract comprising about 10 wt % to about 30 wt % or 5 wt % to about 30 wt % and the solvent comprises water. In one embodiment, the composition further comprises one or more emulsifiers. In one embodiment, the emulsifier comprises about 1 wt % to about 5 wt %, about 2 wt % to about 6 wt %, or about 3 wt % to about 7 wt %.

In one embodiment, a topical oil in water emulsion composition comprising an amount of an extract of raspberry seed, blackberry seed, blueberry seed or pomegranate seed having ellagic acid or ellagitannin effective to lighten human skin and a solvent is provided. In one embodiment, the extract is a raspberry seed extract. In one embodiment, the composition has about 10 wt % to about 30 wt %, or about wt % to about 20 wt % of the extract. In one embodiment, the composition further comprises one or more emulsifiers. In one embodiment, the one or more emulsifiers comprise about 2 wt % to about 5 wt %, about 4 wt % to about 10 wt %, or about 5 wt % to about 15 wt % of the composition. In one embodiment, the composition further comprises an emollient, a buffer, or both. In one embodiment, the solvent comprises water.

The invention will be further described by the following non-limiting examples.

Example I

In one embodiment, the cold press process uses only mechanical pressure to crack and rupture oleosomes, micro sized capsules in the seed, which contain lipids or oil soluble compounds. When the oleosomes are ruptured, the liquid oils flow away from the solid seed material. In one embodiment, no solvents or other additives are used in the cold press process. When only mechanical pressure is used, the lipids or oils are extracted from the seed at roughly room temperature and always less than 100° F. In one embodiment, no external heat or other materials are used. The cold press process creates two product flows, the oil and residual seed fiber or seed meal. Since the lipids make up a smaller portion by weight of the seed, the remaining seed meal or seed fiber make up majority of material produced in the cold press process. The range of seed oil content, oil yield and seed fiber yield from red raspberry, black raspberry, red and blackberry is as follows:

| Seed | Oil Content | Oil Yield rate | Meal Yield Rate |
|---|---|---|---|
| Blackberry | 12-15% | 10-11.5% | 84-85% |
| Black Raspberry | 15-17% | 11-12.5% | 83-85% |
| Red Raspberry | 11-15% | 7-12.5% | 83-85% |

The fatty acids of the raw unrefined cold extracted lipids are as follows:

Fatty Acid Analysis Cold pressed Seed Oils

| | Black Raspberry | Red Raspberry | Black Berry |
|---|---|---|---|
| Saturated fats | 5% | 5% | 5% |
| Oleic | 11% | 12% | 14% |
| Linoleic | 53% | 53% | 58% |
| Linolenic | 30% | 29% | 15% |

Nutrition Profile Seed Meals

| | Black Raspberry | Red Raspberry | Black Berry | Units |
|---|---|---|---|---|
| Calories | 394 | 401 | 411 | calories/100/g |
| Total Fat | 4.25 | 5.4 | 5.8 | % |
| Sodium | 9.1 | 6.7 | 3.1 | mg/100 g |
| Total Carbs | 79 | 78 | 78 | % |
| Total Dietary Fiber | 72 | 71 | 73 | % |
| Protein | 10 | 10 | 12 | % |
| Total Carotenes | 68.3 | | 41 | IU/100 g |
| Calcium | 306 | 206 | 179 | mg/100 g |
| Iron | 9.3 | 6.9 | 7.4 | mg/100 g |
| Moisture | 4.7 | 4.7 | 2.5 | % |

Exemplary ellagic acid content in seed meals was:

| | Total Ellagic Acid mg/g |
|---|---|
| Black Raspberry Flour | 14.15 |
| Red Raspberry Seed Flour | 10.01 |
| Pomegranate Seed Flour | .09 |

The above results for ellagic acid content in the seed meal were noteworthy because they were significantly higher than what has been reported in scientific literature for the concentration of ellagic acid in the fruit, e.g., ellagic acid content for red raspberry fruit at 0.024 mg/g. The cold press derived seed meal has an ellagic acid concentration more than 400 times greater than the fruit.

A 2.5 gram sample of a red raspberry seed extract in a dry powder form was split into two fractions, one combined 1.25 grams of the dry extract with 11.25 grams of water to create a 10% aqueous solution of the extract. The extract did not completely go into solution in water as some portion was not soluble. Combining 1.25 grams of the dry extract with about 11.25 grams of Isopropyl alcohol (91%) produced an about 10% alcohol solution. This resulted in what appeared to be a near completely dissolved solution.

Example II—Separation of Compounds From Powder

C18 Solid Phase Extraction. The resuspended powder may be loaded on a $C_{18}$ solid phase extraction column (Extract-Clean brand, standard C18, 50 μm particle size, 60 angstrom pore size, Grace Davidson Discovery Sciences). The column is then washed with water followed by elution with 15% methanol, 25% methanol, and 100% methanol. Fractions are analyzed using analytical HPLC Strong Cation Exchange Chromatography. Fractions may be dissolved in a solution of methanol and water and loaded onto a strong cation exchange column (Redi-Sep Rf SCX brand, silica based, 40-63 μm particle size, 100 angstrom pore size, Isco-Teledyne) and eluted with a mixture of methanol and water. Elution is monitored by UV and proceeded until the signal, e.g., at 340 nm, decreased to zero. Analytical HPLC chromatograms may be conducted using diode array UV detection from 250-600 nm.

Preparative Scale High Performance Liquid Chromatography. To further separate components, prep HPLC may be employed. The column may be a Waters Symmetry brand, C8 phase, with 7 μm particle size, and dimensions of 19×150 mm, operated at a flow rate of 12 mL/min. A binary solvent gradient is used for this HPLC separation with solvent A=water+0.1% formic acid and solvent B=methanol+0.1% formic acid. Solvent composition at various times was as follows, time (percent B): initial (10% B), 50 min. (35% B), 80 min. (60% B), 85 min. (80% B), 90 min. (80% B). Individual runs may contain a fraction dissolved in 1:1 water/methanol to a volume of 1 mL. The progress of the separation is followed using UV detection, e.g., detection at 255 and 340 nm. Eluent is collected in tubes at 2 minute intervals and the contents of those tubes pooled according to their UV profile to. Evaporation of the solvent from these fractions may yield dry powders. Analytical HPLC chromatograms are conducted with a diode array UV from 250-600 nm.

Analytical Scale High Performance Liquid Chromatography. As a final purification step, fractions may be separated by analytical HPLC.

Example III—Compounds From Seed Powder

The powder is mixed with 70% methanol/30% water solution (100 mL) for 30 minutes. Then Celite (1 g) may be stirred in and the mixture was vacuum filtered through a pad of Celite. Solvents are removed under vacuum. This material is separated using preparative HPLC using the following column: Waters Symmetry brand, C8 phase, with 7 μm particle size, and dimensions of 19×150 mm, operated at a flow rate of 12 mL/min. A binary solvent gradient is used for this HPLC separation with solvent A=water+0.1% formic acid and solvent B=methanol+0.1% formic acid. Solvent composition at various times is as follows, time (percent B): initial (10% B), 50 min. (35% B), 80 min. (60% B), 85 min. (80% B), 90 min. (80% B). Individual runs may contain about 40 mg of seed extract dissolved as a solution of water/methanol to a volume of 1 mL. The progress of the separation is followed using UV detector at 255 and 340 nm. Eluent is collected in tubes at 2 minute intervals and the contents of these tubes are pooled according to their UV profile.

Example IV-Comparison of Different Seed Powders

Methods and Materials
Seed Materials:

Seed powders were obtained from Botanic Innovations. They were produced by mechanically pressing seeds in their NatureFRESH Cold Press process, which removes most of the seed oils. The solid seed materials that remain after pressing can be ground to a powder that retains a small percentage of seed oils (around 5-10%), and all of the other compounds in the seeds that are not dissolved in the oils. Seed powders from fruits including cranberry, pomegranate, red raspberry, black raspberry, blackberry, blueberry, and watermelon were studied along with the dried skins of cranberries. Seed powders from vegetables including broccoli, radish, tomato and carrot were also studied.

Extraction Solvents and Criteria:

The following criteria were applied when screening extraction protocols to serve as the second level of purification (after cold pressing by Botanic Innovations).

1. The extraction process should use inexpensive and widely accessible solvents. Solvents with low flammability and low toxicity were desirable. Therefore, the solvents used in this round of purification were water, alcohols, and mixtures of these solvents.
2. The method should be amenable to scaling up and optionally not use highly specialized equipment.
3. The extraction process should produce high yields of extracted substances.
4. The protocol should effectively extract the desired target substances, but leave residual undesired oils behind.
5. The mixtures of seed powders and solvents after extraction are filterable so as to isolate the filtrate containing the desired compounds. Solvents that produced mixtures with fine particulates, or that required multiple passes of filtration, or that frequently clogged filtering media should be avoided.
6. It is desirable to remove the solvent by distillation to isolate the mixture as a solid or concentrated liquid residue. Therefore, solvents with boiling points above 100° C. were avoided.

Chemical Characterization of Extracts by HPLC:

Seed powder extracts were characterized by high performance liquid chromatography (HPLC). After some experimentation, a method was developed that resolved compounds into peaks in runs requiring 45 minutes. The column used was a Waters Symmetry brand with dimensions of 150×3.9 mm. It contained a C8 stationary phase with a 5 μm particle size. A constant flow rate of 1.00 mL/min was used in all experiments. A binary solvent system was used with a gradient elution program. The "A" solvent was deionized water with 0.1% added formic acid. The "B" solvent was pure HPLC grade methanol. The gradient started at 2% B solvent, which was held constant for 5 minutes. The concentration of the B solvent was then increased from 2% to 50% between 2 min. and 20 min. It was increased from 50% to 100% B solvent between 20 min. and 25 min., and then held at 100% B solvent for 5 min. before returning back to 2% B solvent over 5 min. Injection volumes were between 5-10 μL of analyte solution. Peaks were detected by UV absorption using a diode array detector. This provided the full UV spectrum of each peak, which was used to confirm the identity of unknown peaks by comparing the unknown's UV spectrum and retention time to authentic standards that were purchased from commercial sources. Materials that were analyzed for included α-arbutin, β-arbutin, ellagic acid, niacinamide, and raspberry ketone. Retention times of the standards used and their maximum UV absorbing wavelengths (λmax) are listed in Table 1.

TABLE 1

HPLC standard retention times and $\lambda_{max}$ values

| Standard | Retention time (min) | $\lambda_{max}$ (nm) |
|---|---|---|
| α-arbutin | 3.44 | 226, 283 |
| β-arbutin | 3.55 | 226, 283 |
| ellagic acid | 21.87 | 255, 369 (weak) |
| niacinamide | 2.53 | 220, 262 |
| raspberry ketone | 19.38 | 228, 277 |

The use of HPLC with a mass spectrometer detector (LC-MS) may be employed.

Tyrosinase Inhibition Assays:

Extracts were tested for their ability to inhibit the enzyme tyrosinase. This enzyme catalyzes the air oxidation of L-DOPA (colorless) to the compound dopachrome, which is a highly colored intermediate in the production of melanin. The dopachrome molecule absorbs strongly at 475 nm. So, measuring the rate of change of absorption at this wavelength using UV/visible spectroscopy can easily assess the enzyme's activity. The tyrosinase enzyme (from mushroom) was purchased from Sigma-Aldrich as a lyophilized powder with an activity of 5771 units per mg of solid (a unit of activity is defined as the rate at which the enzyme catalyzes the reaction of a standard substrate at a standard concentration). This enzyme (1.0 mg) was dissolved in 0.1 M aqueous pH 7.00 phosphate buffer (28.9 mL) to generate a solution with an activity of 200 units/mg, which was used throughout the assays. The L-DOPA substrate was purchased from TCI America and dissolved in deionized water at a concentration of 7.5 mM. Inhibitors were dissolved in DMSO at various concentrations to test their potency. Assay runs were carried out by pipetting solutions into plastic cuvettes in the following order (typical amounts in parentheses). L-DOPA substrate (100 μL) was added followed by phosphate buffer solution (2.35 mL), and a DMSO solution with dissolved inhibitor or a blank of pure DMSO to act as a control (50 μL). The cuvette was covered with a piece of Parafilm and inverted twice to thoroughly mix the solutions. Next, the enzyme solution was added (500 μL), the cuvette was covered with a piece of Parafilm and inverted twice to thoroughly mix the solutions, and immediately after the cuvette was placed in a UV/visible spectrometer and absorbance was measured at 475 nm every second for 60 seconds. The slope of the line formed by graphing change in absorbance versus time gave the rate in units of AA/second. This rate was converted into units of μmol of L-DOPA consumed per minute (μmol/min).

Results and Discussion

Extractions Using Water

Using pure water was explored in extraction experiments with cranberry seed powder. The advantages of using water were essentially zero cost and toxicity. It is also a very polar solvent and did not extract any residual oils (which are very non-polar compounds) from the seed powders. The limitations of using water were that it gave quite low yields in extractions at room temperature and only dissolved the most polar compounds from the seed powders, leaving most of the medium polarity materials behind. It is possible that this could be improved by heating. Filtering mixtures of water and seed powders also proved to be rather difficult. Simply filtering the mixture through inexpensive filter paper by gravity or mild vacuum was unsuccessful. One solution that worked was mixing in filtering media (diatomaceous earth) and then vacuum filtering through a bed of the same filtering medium. To completely clarify the mixture, an additional treatment with activated carbon and further vacuum filtering through a bed of diatomaceous earth was effective. Given the limitations of water extraction, it was not used extensively. One exception was the use of sodium hydroxide solutions in water to extract pomegranate seed powder, which contained significant amounts of the targeted compound ellagic acid. Ellagic acid is only slightly soluble in water at neutral pH, but at high pH it becomes very water soluble. Therefore, 1 M aqueous sodium hydroxide solution was used to extract this material from pomegranate seed powder. After filtering away the solid seed material the solution was acidified to pH=4 by addition of 1 N HCl. A small amount of solid developed, which was filtered with some difficulties. An HPLC chromatogram of this solution is shown in FIG. 1.

Peak retention times are shown in minutes above and offset to the right of each peak in chromatograms. Ellagic acid is the large peak at 21.598 minutes, which was confirmed by comparing its retention time to that of an authentic standard and comparing its UV spectrum to the standard. The peak at 4.652 min is an unknown compound in pomegranate seeds.

Extractions Using Ethanol

Figure 2:
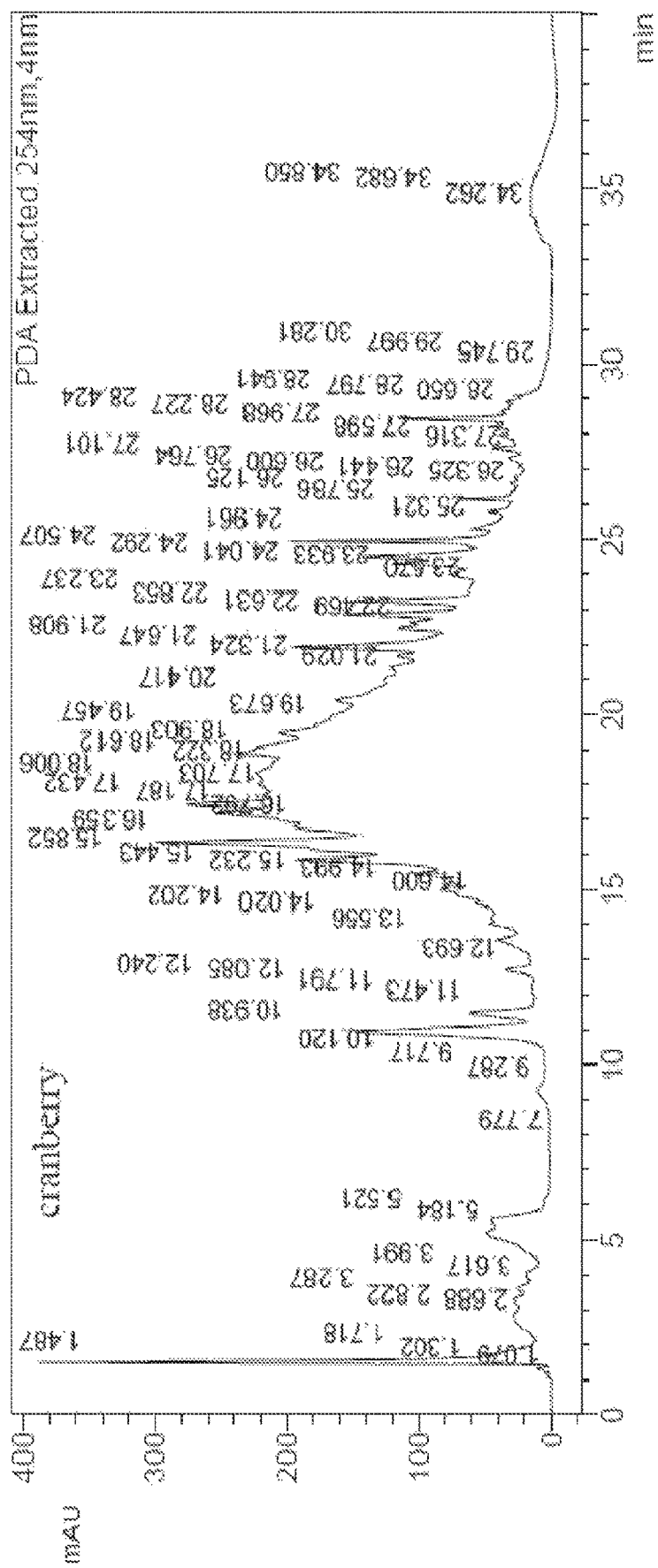
FIG. 2. Chromatogram of cranberry seed powers extracts with ethanol at 254 nm.
Figure 3:
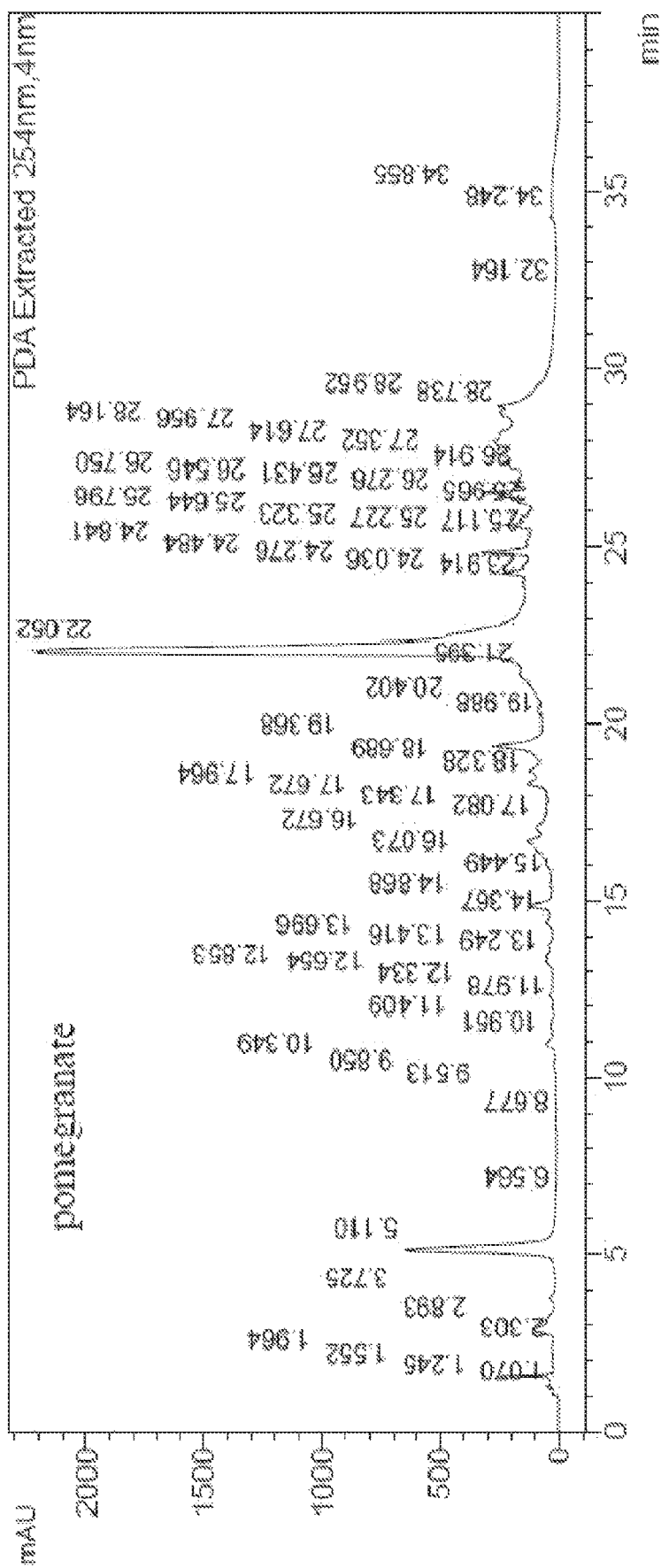
FIG. 3. Chromatogram of pomegranate seed powers extract with ethanol at 254 nm.
Figure 4:
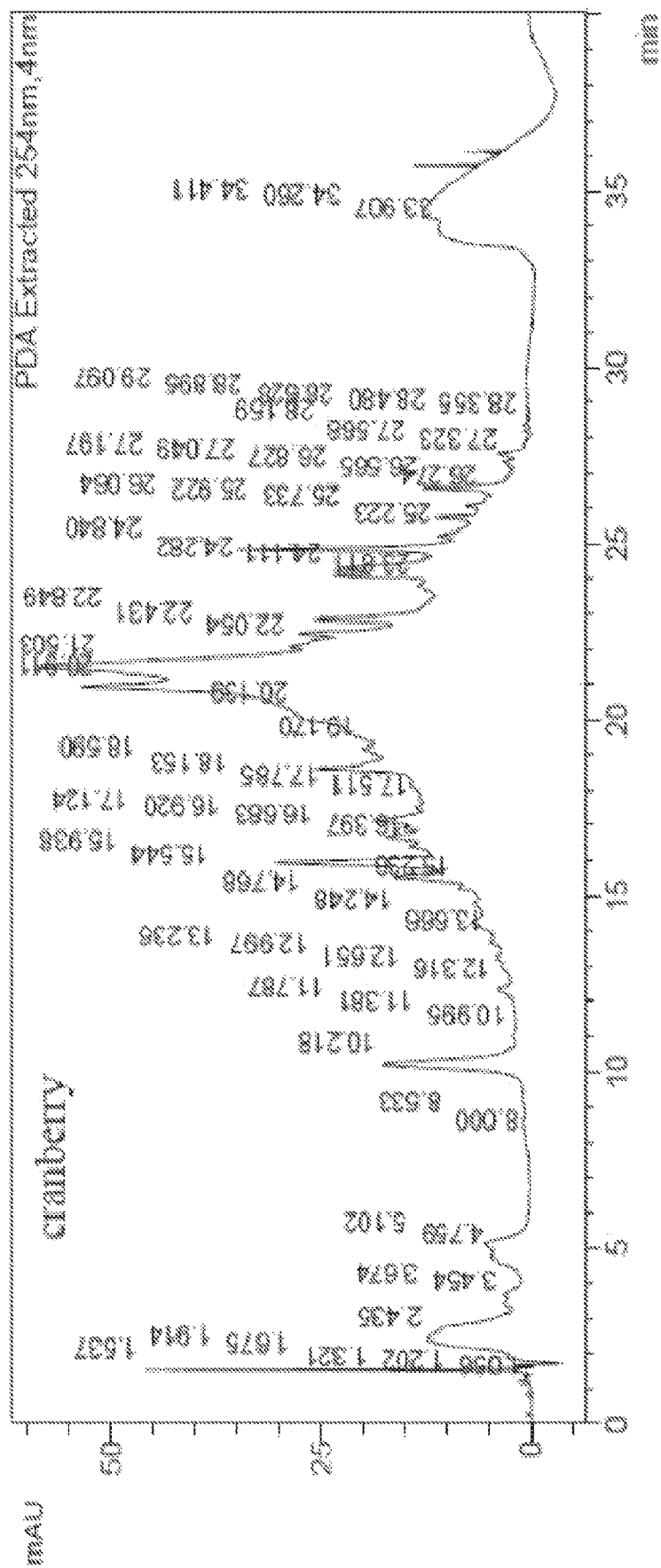
FIG. 4. Chromatogram of 70:30 methanol/water extract of cranberry seed powder at 254 nm.
Figure 5A:
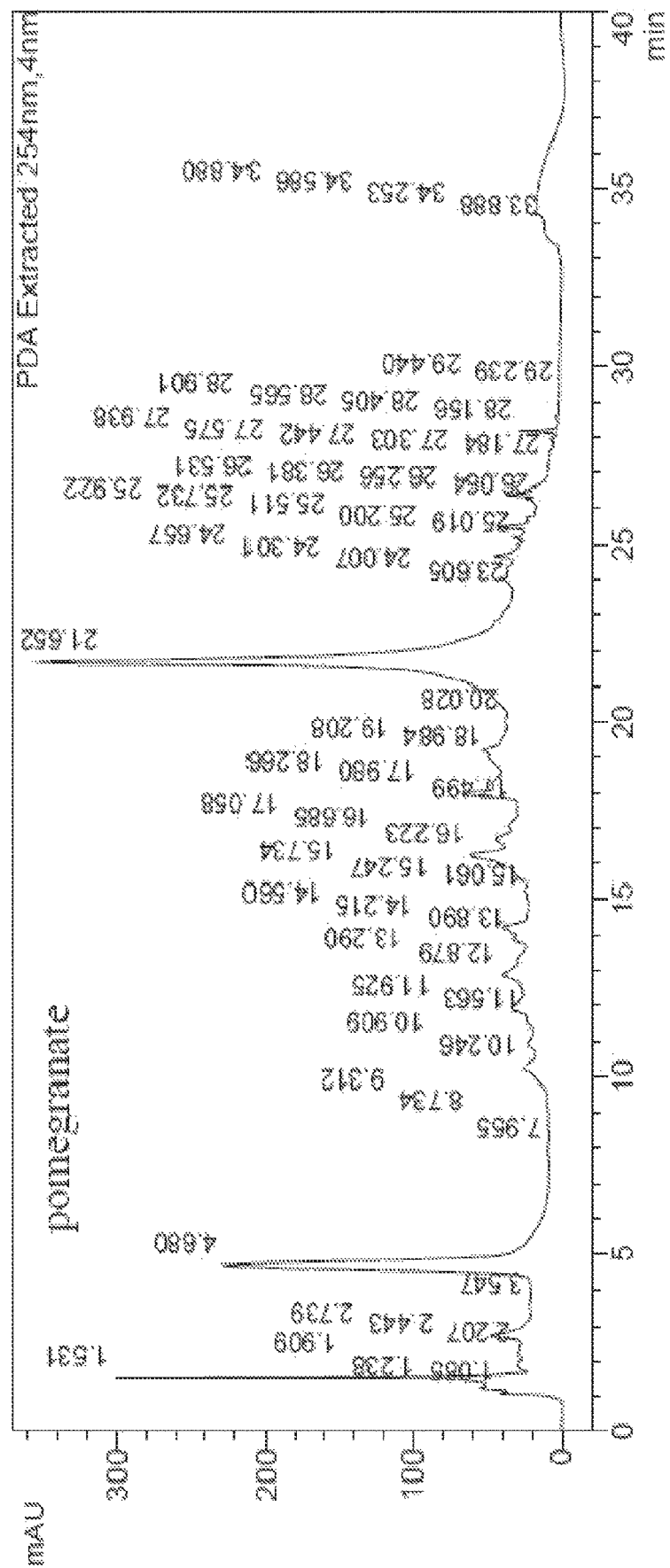
FIG. 5. Chromatograms of 70:30 methanol/water extracts of seed powders from pomegranate (top), red raspberry (middle) and black raspberry (bottom) at 254 nm.
Figure 5B:
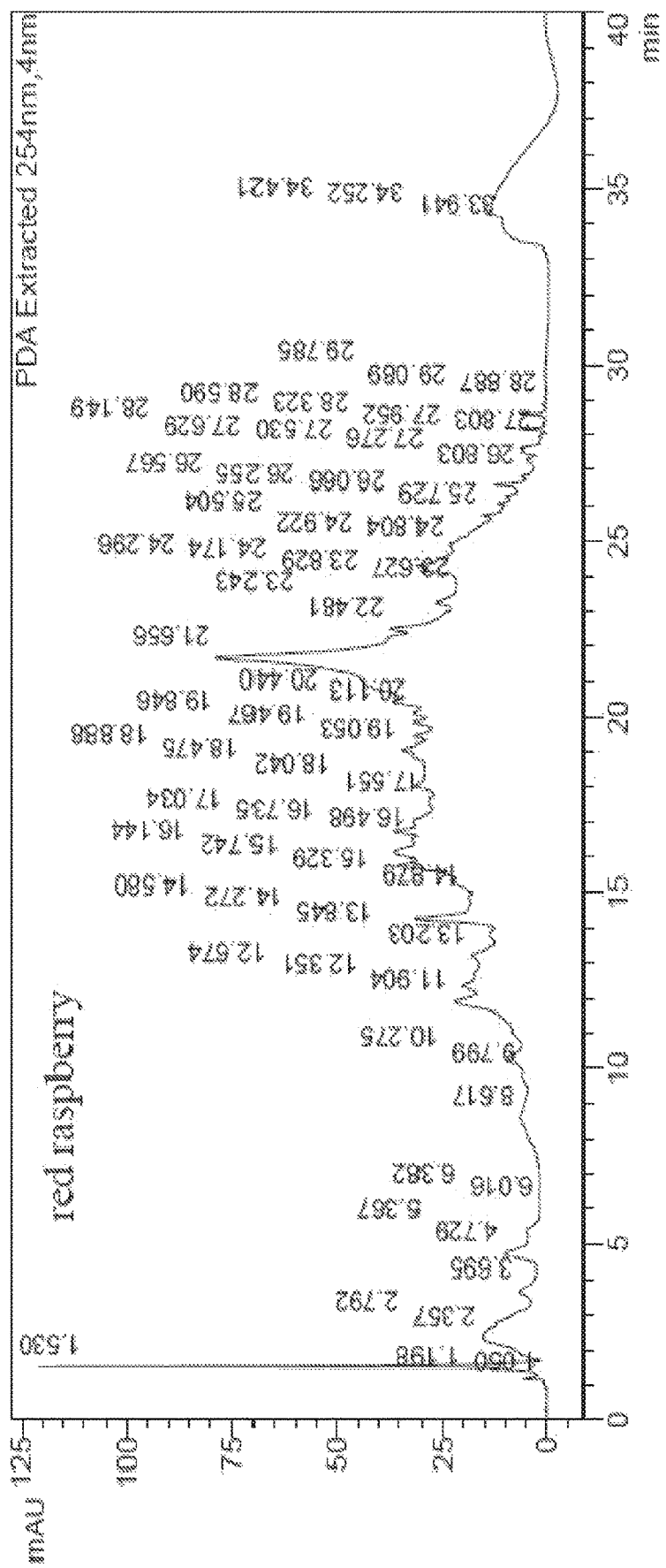
Figure 5C:
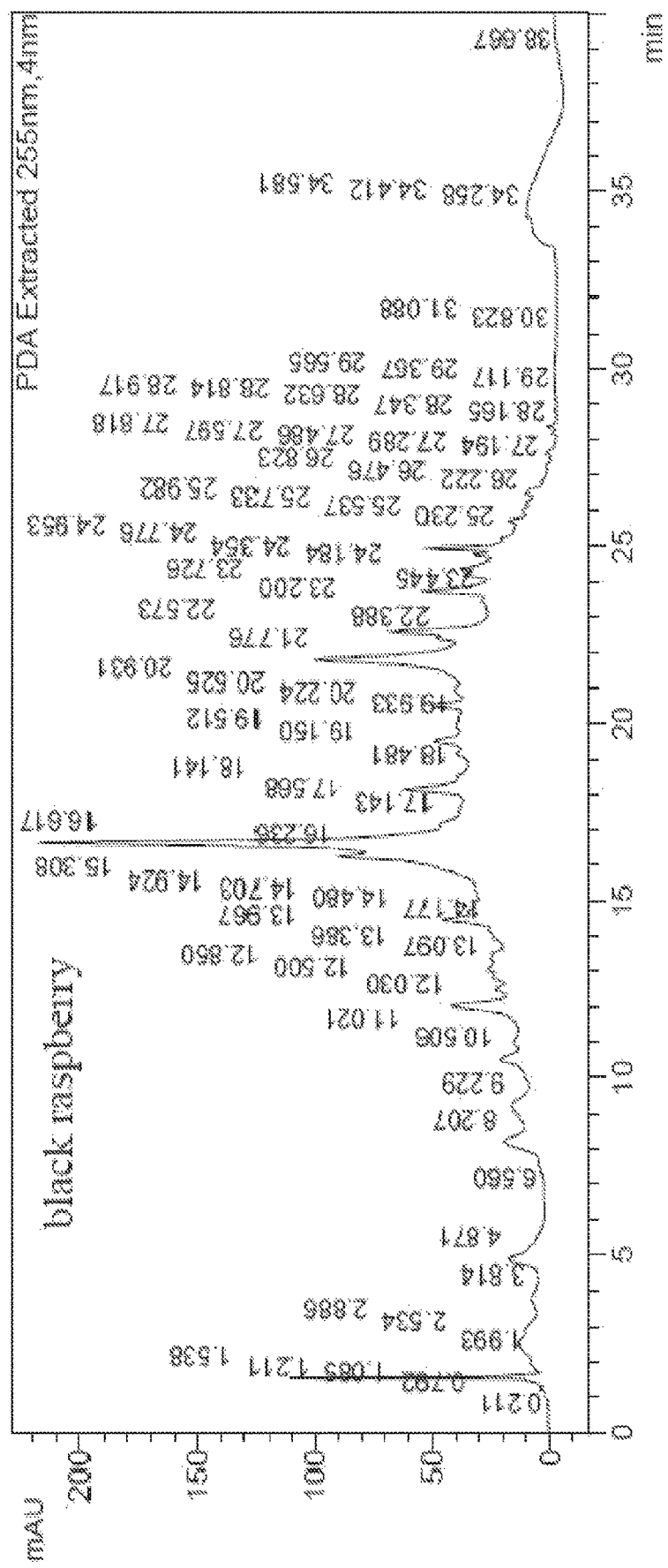
Figure 6A:
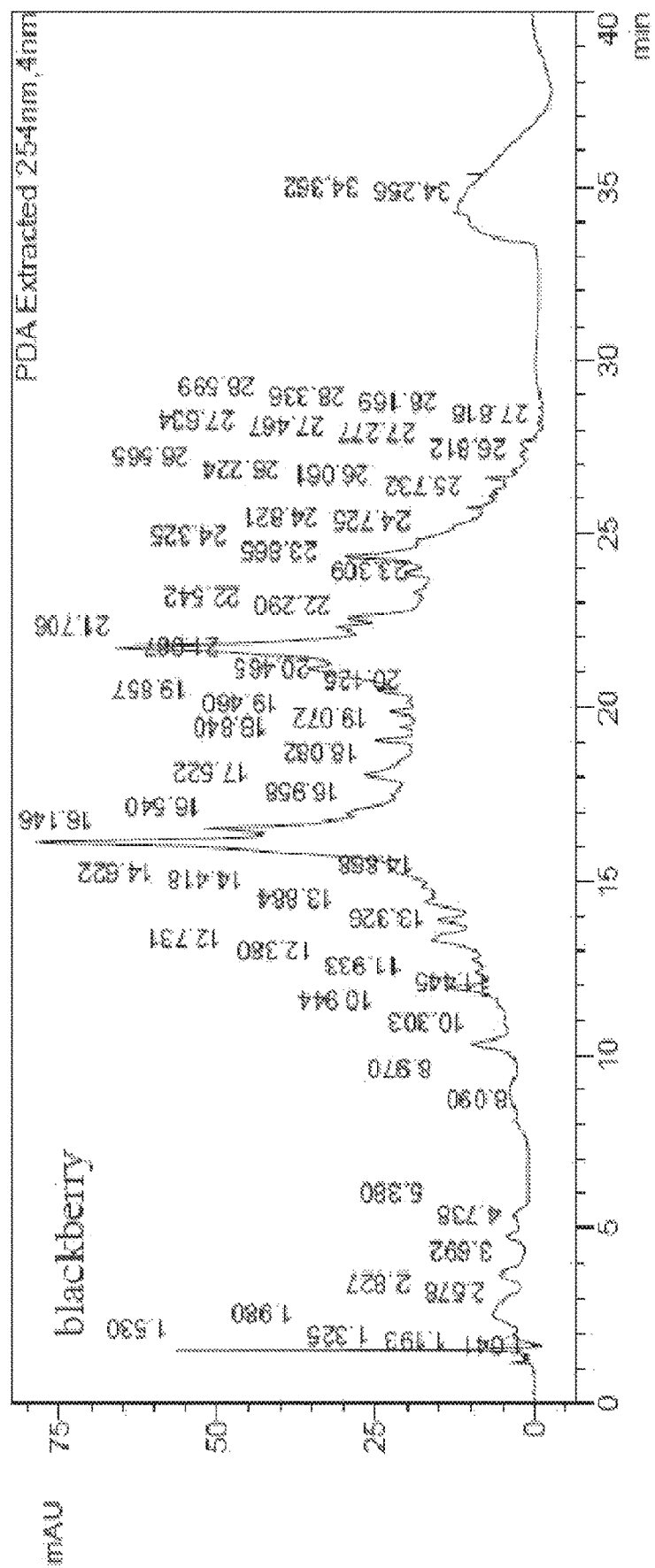
FIG. 6. Chromatograms of 70:30 methanol/water extract of seed powders from blackberry (top), watermelon (middle), and blueberry (bottom) at 254 nm.
Figure 6B:
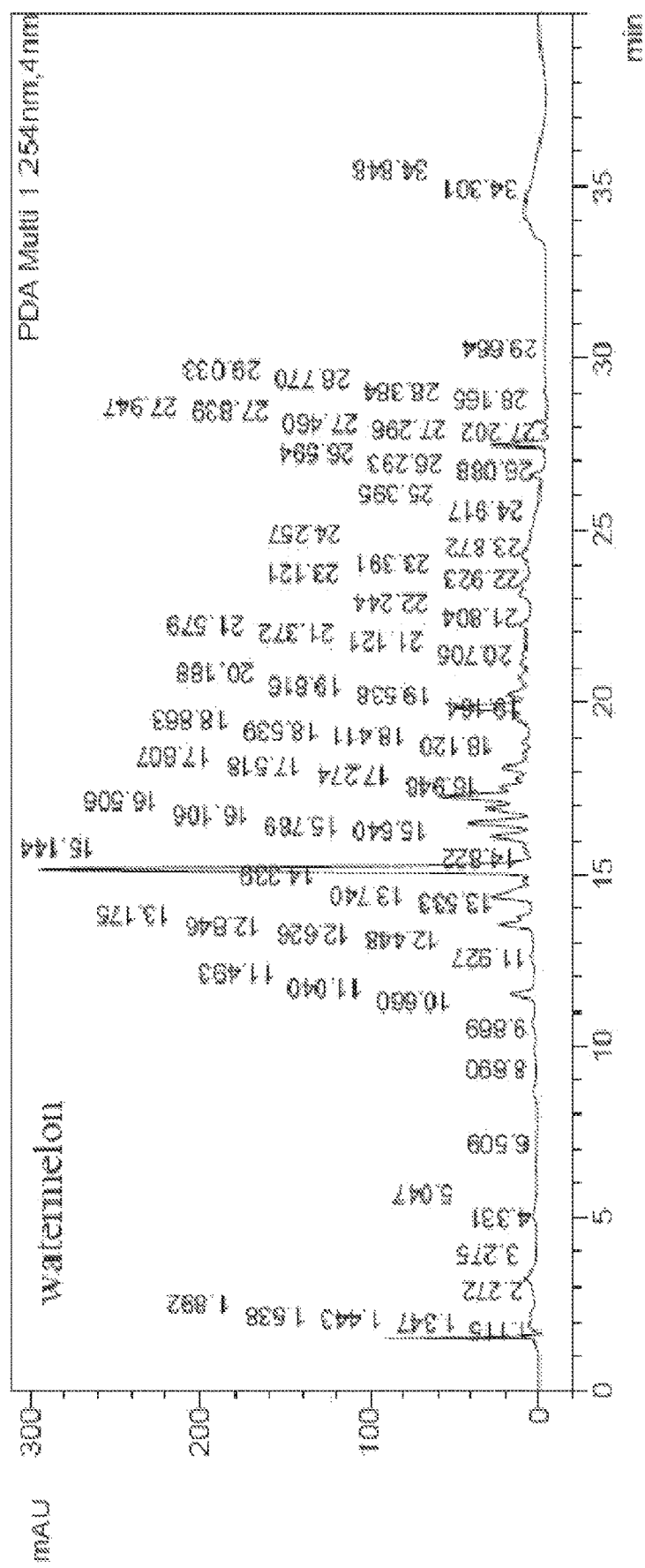
Figure 6C:
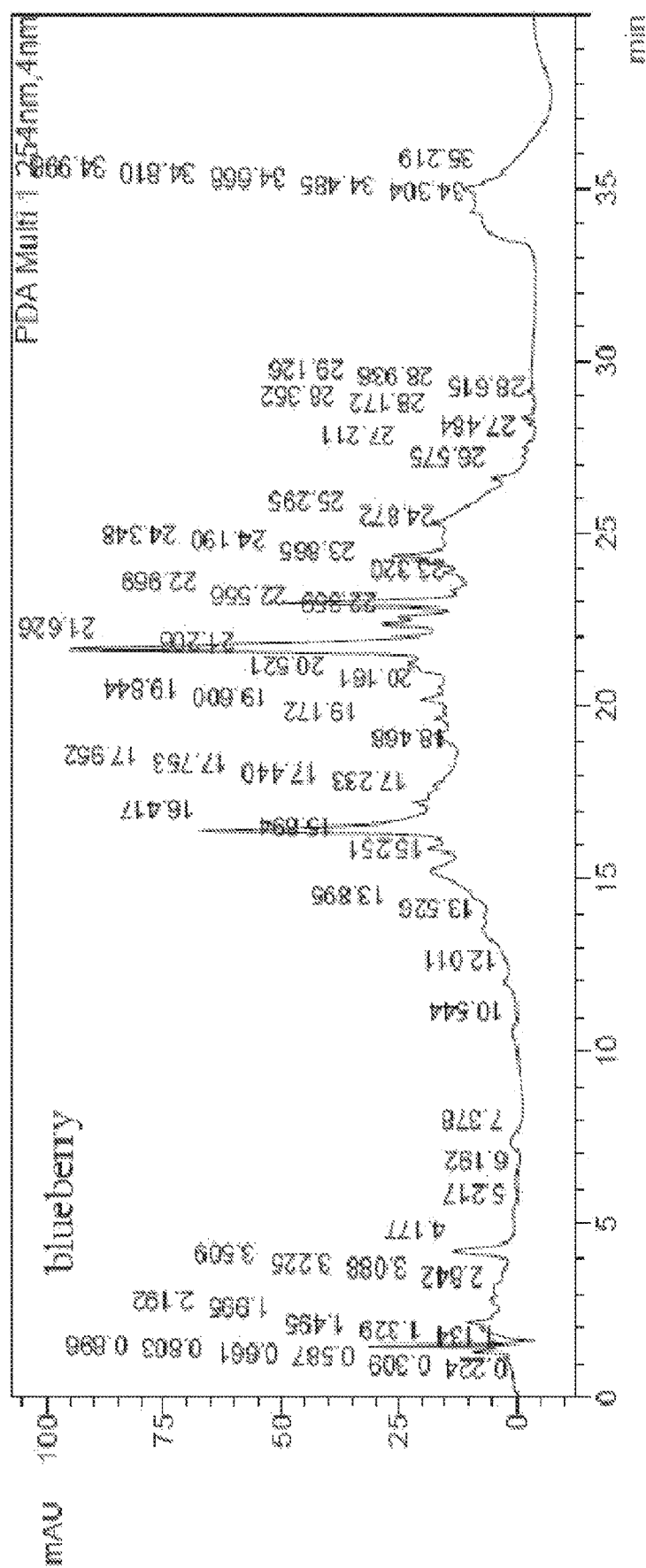
Figure 7:
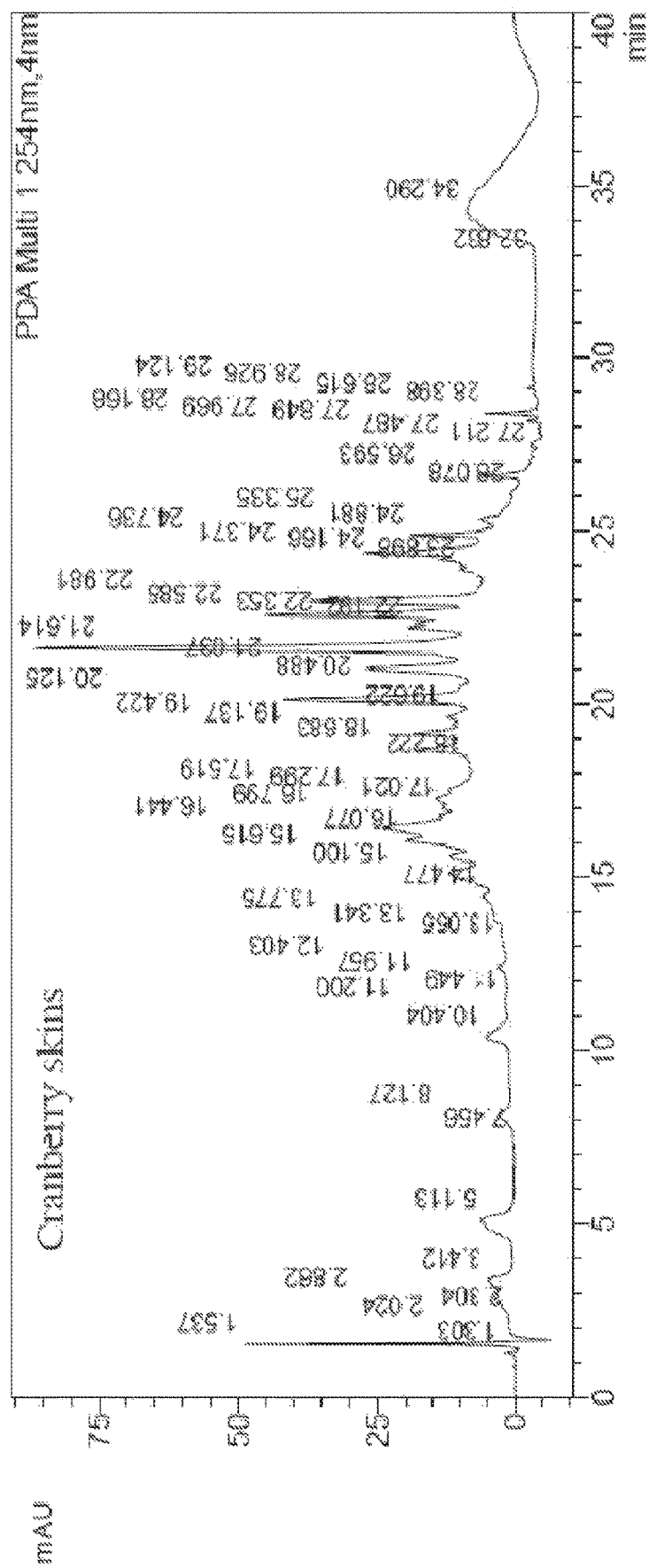
FIG. 7. Chromatogram of 70:30 methanol/water extract of dried cranberry skins at 254 nm.

Pure ethanol was also briefly explored in extraction experiments with cranberry and pomegranate seed powders. Each seed material (100.0 g) was mixed with denatured ethanol (400 mL) for 2 hours, and then filtered. These filtrations proceeded smoothly. Evaporation gave residues that were very oily. To separate the residual seed oil from other compounds of interest the residues were washed with petroleum ether (50 mL). This solvent dissolved the oils and gave other compounds as a precipitate, which was filtered. The yield for cranberry seed material was 0.495 g (0.5%). These solid samples were hygroscopic (water absorbing), and became syrupy on exposure to the air. Adding methanol (2.5 mL) to each gave a precipitate that was insoluble in all common solvents and a filtrate. HPLC chromatograms of the filtrates from these processes are shown in FIG. 2. The cranberry extract is a very complex mixture with numerous peaks, many of which are overlapping. The pomegranate extract in contrast was much simpler and contained the same two major UV-active peaks as in the aqueous base extract of this material shown in FIG. 1. The retention times of the peaks are shifted slightly in the two chromatograms, but analysis of their UV spectra showed that they are the same. The large peak at 22.054 min in pomegranate is ellagic acid.

Extractions With 70:30 Methanol/Water

Mixtures of pure water and pure alcohol as extraction solvents were examined. One highly effective combination was the use of a solution of 70% methanol and 30% water (volume to volume). This solvent system seems to have the right polarity to provide good yields of desired materials and no problems with co-extraction of undesirable seed oils. Furthermore, extractions with this solvent system were easily filterable. The protocol used 5.00 g of seed powder, which was suspended in deionized water (70 mL), with stirring. Methanol was added (30 mL) and the mixture was stirred 16 hours at room temperature. Vacuum filtering the mixture through Whatman #1 filter paper quickly gave a clear solution, which usually was tinted a red or yellow color. These solutions were analyzed directly by HPLC. They were then concentrated under reduced pressure on a rotary evaporator at 40° C. to 25 mL, which removed most of the methanol and left a solid suspension in water. Evaporating further in a stream of air or by freeze drying gave the residues listed in Table 2. All of the extracts were hygroscopic and absorbed between 0.6% and 1.3% of their mass in water upon standing at room temperature. This tended to give them a very thick syrupy consistency, which was more pronounced in certain extracts and less pronounced in others as noted in Table 2. Table 2 also lists the mass of each extract and percent mass recovery (yield) based on 5.00 g of starting seed powder, or dried cranberry skins. Yields in this process were excellent compared to previous extractions in either pure water or pure ethanol.

TABLE 2

Fruit Seed Extract Mass, % Yield, Color, and Morphology

| Seed Source | Extract Mass | % Yield | Color | Morphology |
| --- | --- | --- | --- | --- |
| Cranberry | 0.65 g | 13% | dark red | viscous liquid |
| Pomegranate | 0.89 g | 18% | yellow/brown | viscous liquid |
| Red Raspberry | 0.42 g | 8.4% | salmon | solid |
| Black Raspberry | 0.33 g | 6.7% | maroon | solid |
| Blackberry | 0.48 g | 9.6% | dark purple | viscous liquid |
| Watermelon | 0.80 g | 16% | orange | viscous liquid |
| Blueberry | 0.77 g | 15% | dark blue/purple | sticky solid |
| Cranberry skins | 0.99 g | 20% | red | viscous liquid |

Chromatograms of the eight fruit extracts are shown in FIGS. 4-7. Ellagic acid was present in many of the extracts. There doesn't appear to be a significant quantity of either alpha or beta arbutin present in cranberry seed powder, or any of the other seed powders studied thus far. The other target compounds, niacinamide and raspberry ketone, were also not major components of the seed extracts.

In addition to fruit seed powders, four vegetable seed powders from Botanic Innovations were extracted and studied. As with the fruit seed materials, these vegetable seed powders were extracted using a 70:30 (volume/volume) solution of methanol and water for 16 h with room temperature stirring. Table 3 lists the materials investigated thus far along with the mass of extract obtained from 5.00 g of seed powder, the percent yield of the extraction, the color of the extract after solvents were removed, and the morphology of solvent-free material.

TABLE 3

Vegetable Seed Extract Mass, % Yield, Color, and Morphology

| Seed Source | xtract Mass | % Yield | Color | Morphology |
|---|---|---|---|---|
| Broccoli | 0.87 g | 17% | tan | solid |
| Radish | 1.01 g | 20% | tan | solid |
| Tomato | 0.43 g | 8.7% | light yellow | solid |
| Carrot | 0.57 g | 11% | amber | hygroscopic solid |

Figure 8A:
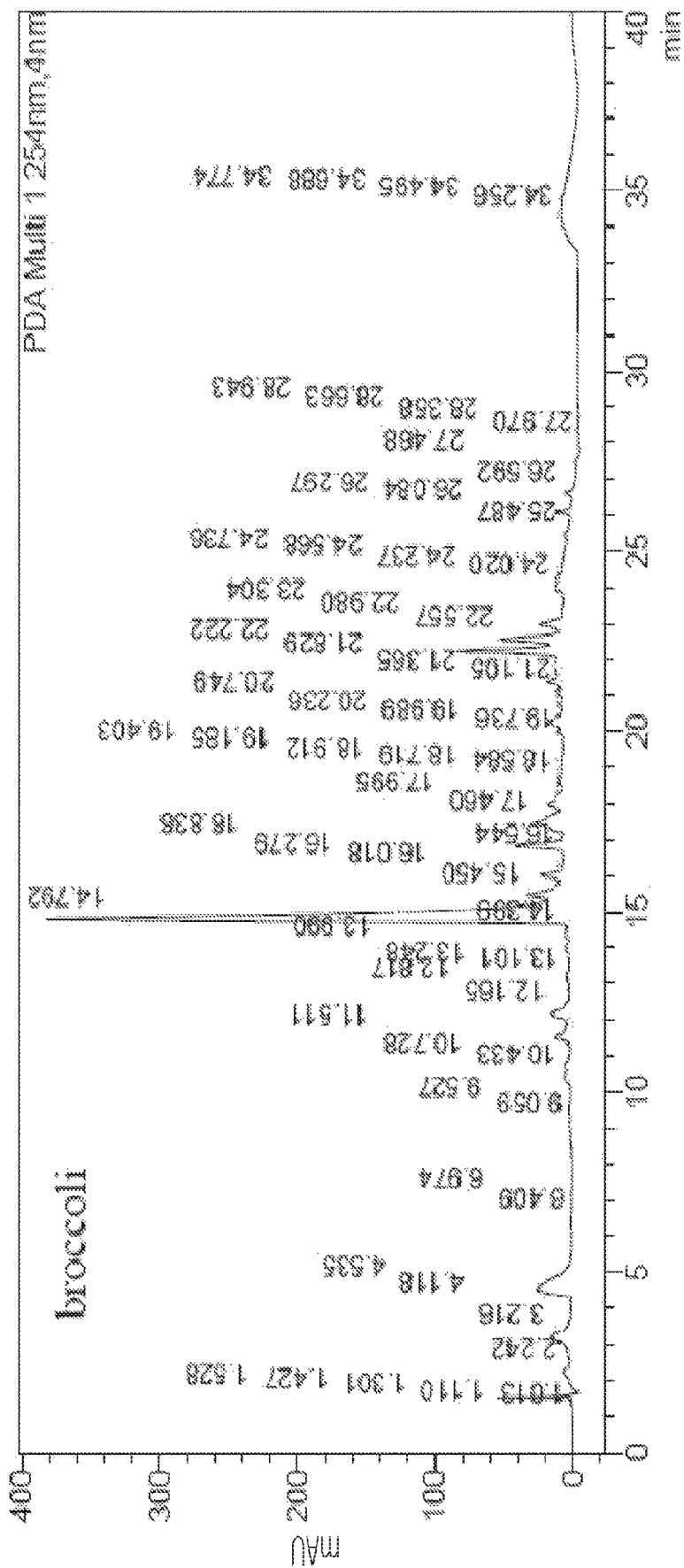
FIG. 8. Chromatograms of 70:30 methanol/water extract of seed powders from broccoli (top), radish (middle), and tomato (bottom) at 254 nm.
Figure 8B:
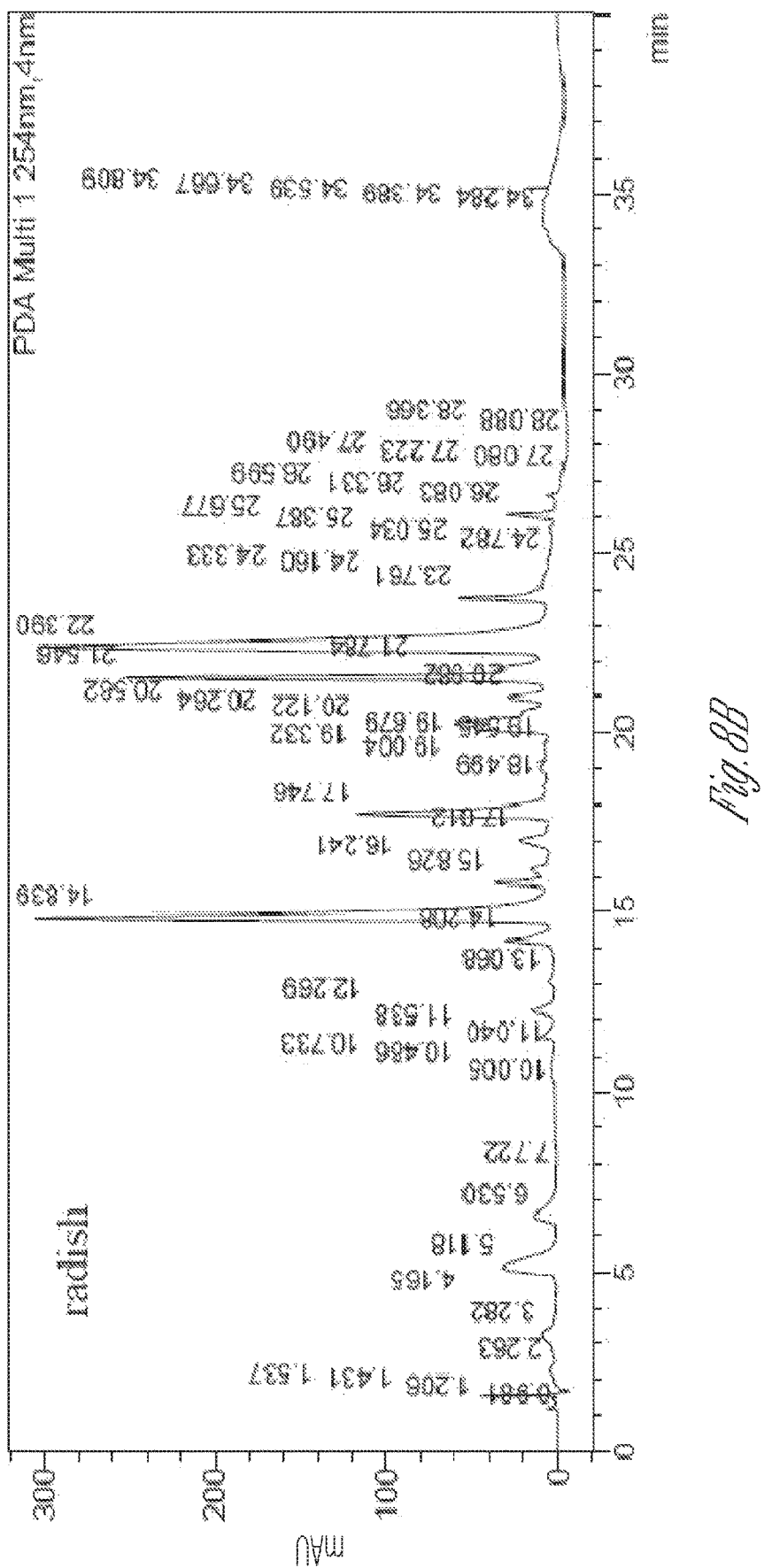
Figure 8C:
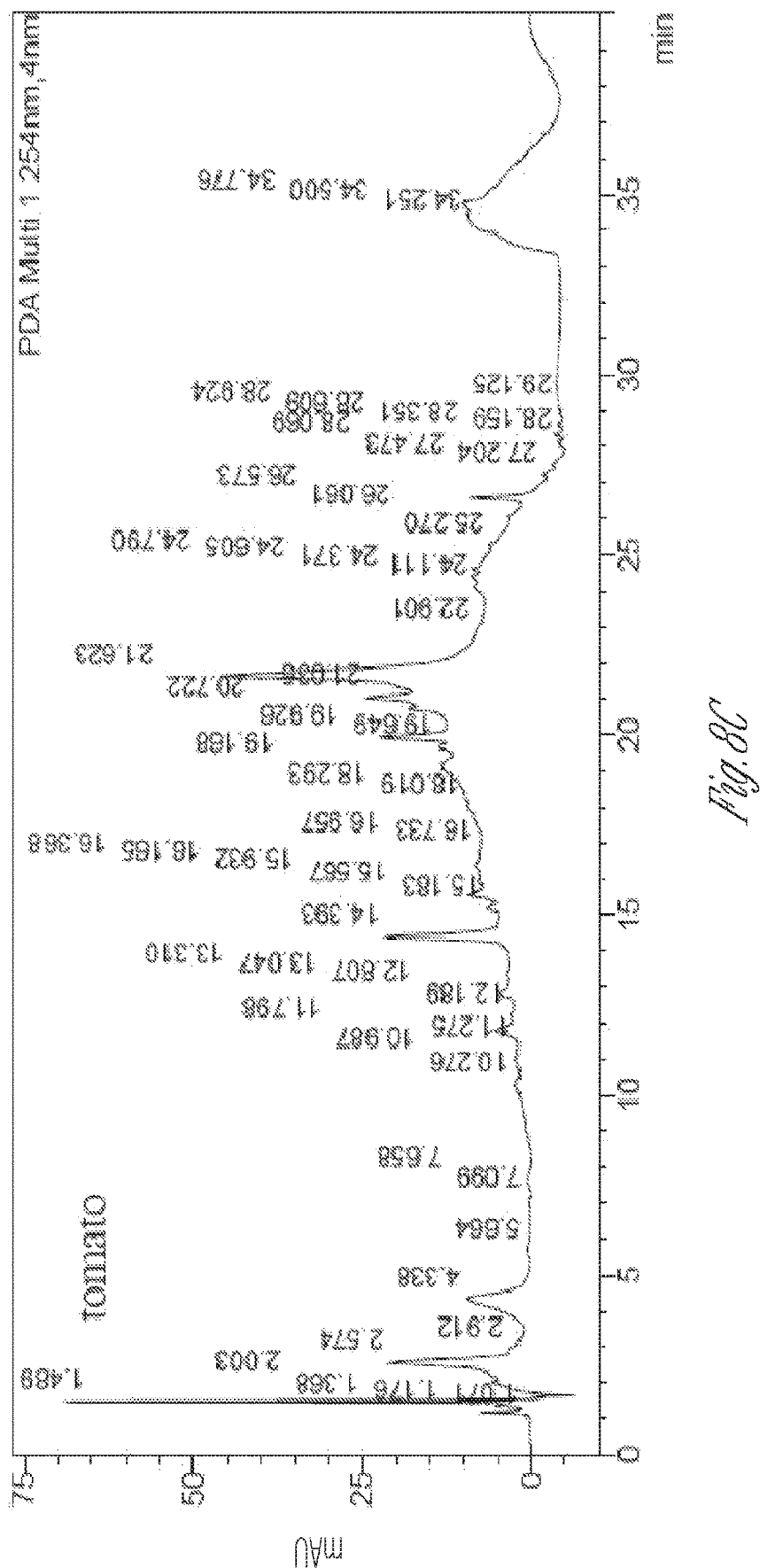
Figure 9:
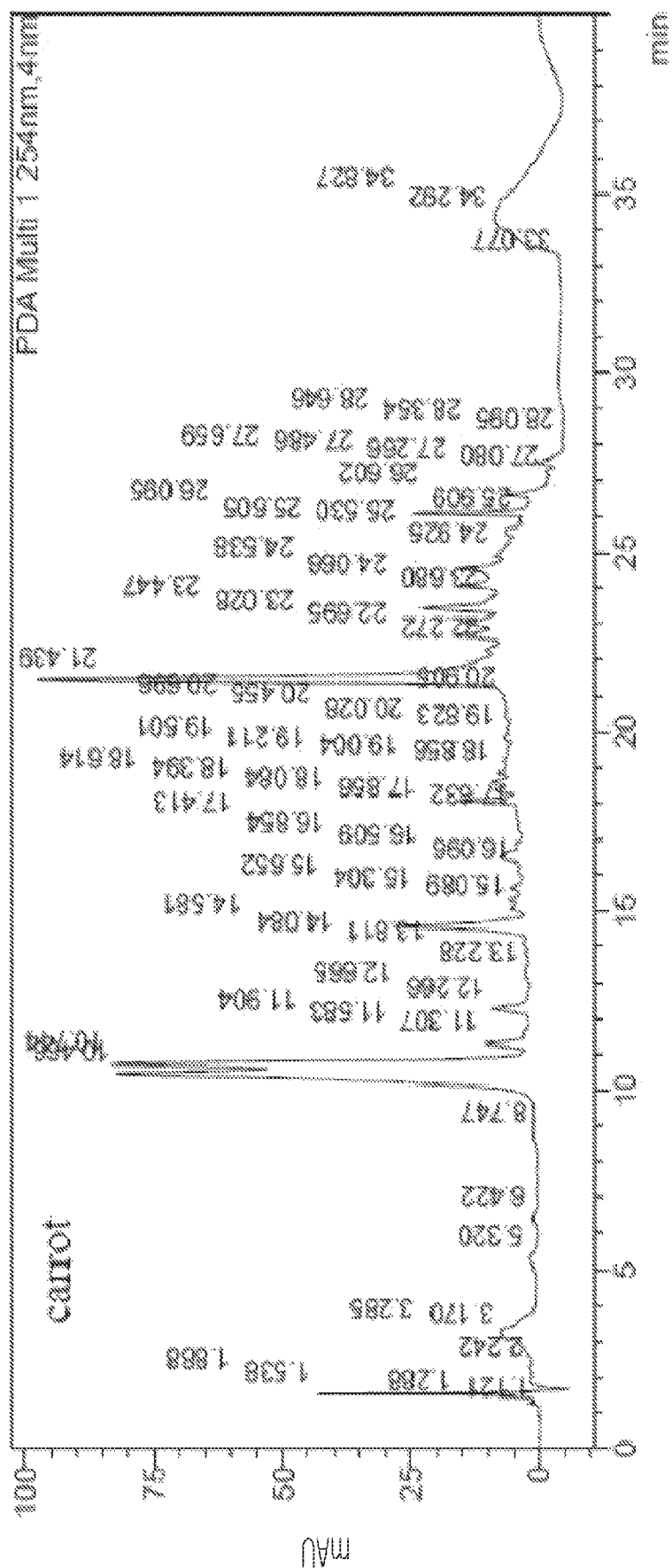
FIG. 9. Chromatogram of 70:30 methanol/water extract of carrot seed powder at 254 nm.

The vegetable seed powder extracts were also characterized by HPLC with UV detection. FIG. 8 shows the HPLC chromatograms for broccoli, radish and tomato extracts, and FIG. 9 shows carrot extract. Broccoli and radish showed one major common peak, which could be sulforaphane. This will be explored in future work. Both of these vegetables are from the brassica (mustard) family and compositional similarities were therefore expected. Carrot and tomato are quite different compositionally from other vegetable and fruit materials.

Expedited Extractions With 70:30 Methanol/Water

To speed up the preparation process, experiments were carried out using shorter extraction times using red raspberry seed powder as a model. The yields and compositions of these materials were compared to the previous results with 16 hour extraction times. It was found that the two hours of extraction time with 70:30 methanol/water gave identical results to the longer overnight protocol used previously. The yield and morphology of material generated in two hours matched the 16 hour extraction and there were no perceivable differences in the HPLC chromatograms of these materials. It was also found that the ability of the extracts to inhibit tyrosinase enzyme was identical, which will be discussed in the following section. It is possible that even shorter extraction times may be achievable without a decrease in performance. The efficiency advantage of shorter procedures will be important in large scale production of extracts, which is anticipated in the future.

Figure 10:
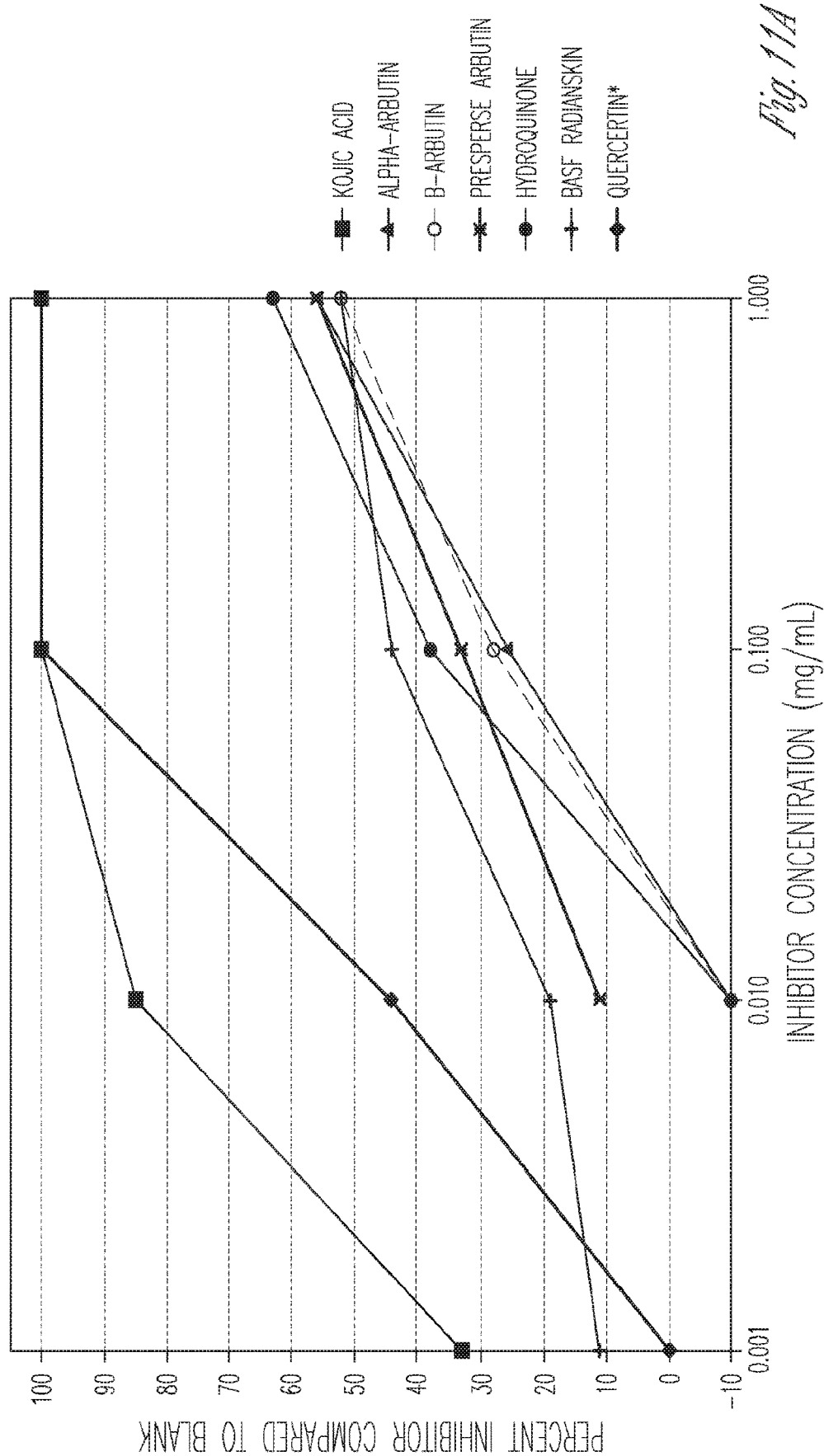
FIG. 10. Tyrosinase percent inhibition data.

Tyrosinase Inhibition Studies:

The extracts in Tables 2 and 3, prepared from 70:30 methanol/water, were tested for their ability to inhibit tyrosinase at concentrations of 1.0 mg/mL, 0.1 mg/mL, 0.01 mg/mL, and in some cases 0.001 mg/mL. This inhibition data is reported in Table 4. For comparison several other known tyrosinase inhibitors including kojic acid, alpha-arbutin, beta-arbutin, hydroquinone, and quercetin were tested. Kojic acid is often used in tyrosinase inhibition studies as a benchmark inhibitor for comparison with other inhibitors. I included beta-arbutin and hydroquinone due to their relevance in skin whitening applications. Additionally, several commercial skin whitening agents were also tested. These included a product called Radian Skin from BASF, and an arbutin material sold by the company Presperse. The reference compound ellagic acid was highly insoluble in the enzyme assay and could not be tested at the same levels as the other inhibitors for that reason. Even highly dilute samples of ellagic acid were not sufficiently soluble. The compound quercetin also had similar solubility limitations, but not as severe. Finally, a mixture of red raspberry and tomato extracts (FIG. 10) was tested to look for possible synergistic effects in mixtures on two quite different materials. The presence of negative inhibition values is simply a reflection of the error of the test, which is likely around +/−5%.

Percentage inhibition values were calculated by taking the rate of the blank run with no inhibitor minus the rate of the inhibited sample and then dividing that value by the blank rate and multiplying by 100. In equation form this is:

Percentage inhibition=[[blank rate−inhibitor rate]/blank rate]*100

Figure 11:
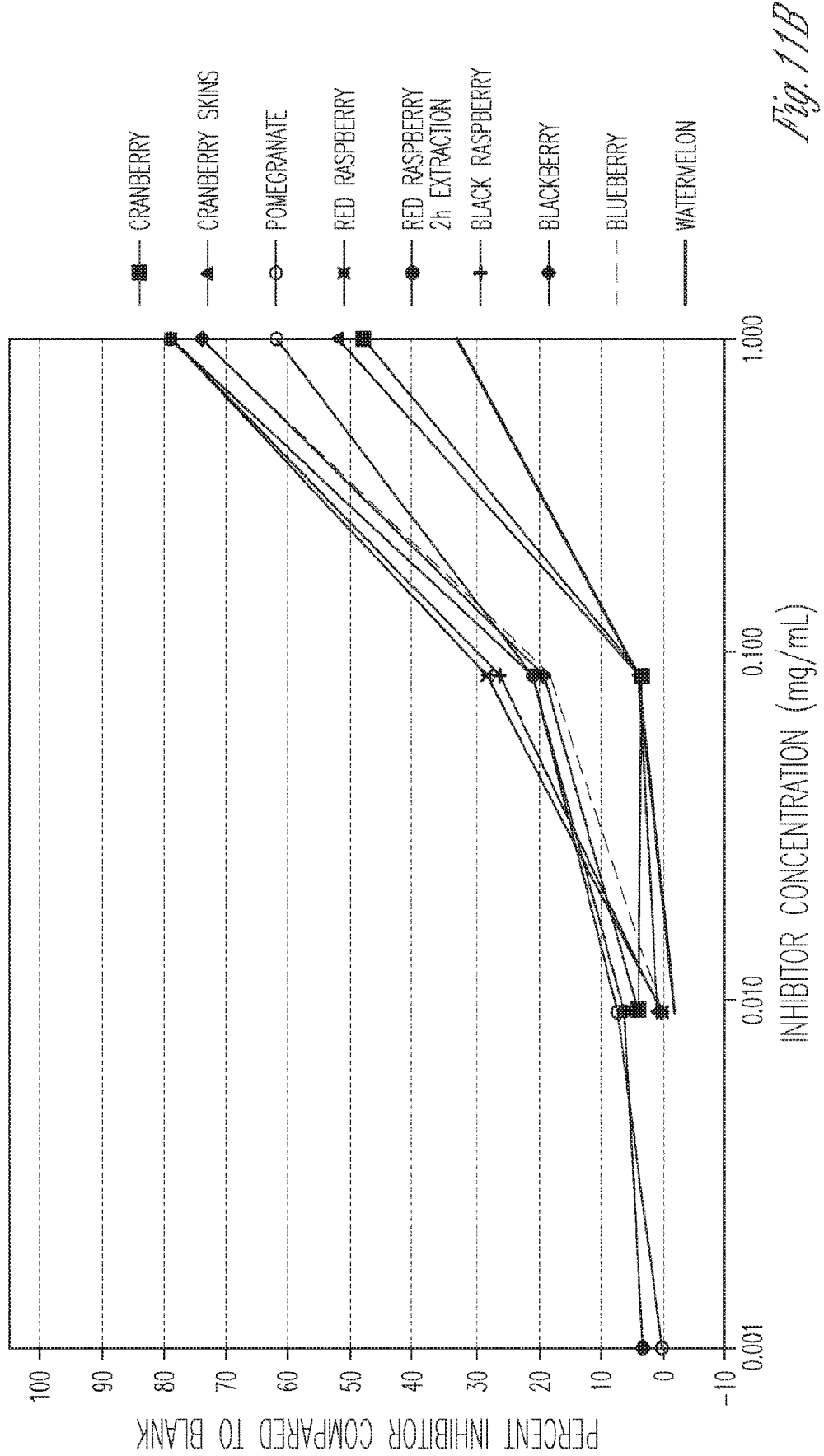
FIG. 11. Percent inhibition of known inhibitors and commercial skin whiting products (top), and fruit extracts (bottom).
Figure 12:
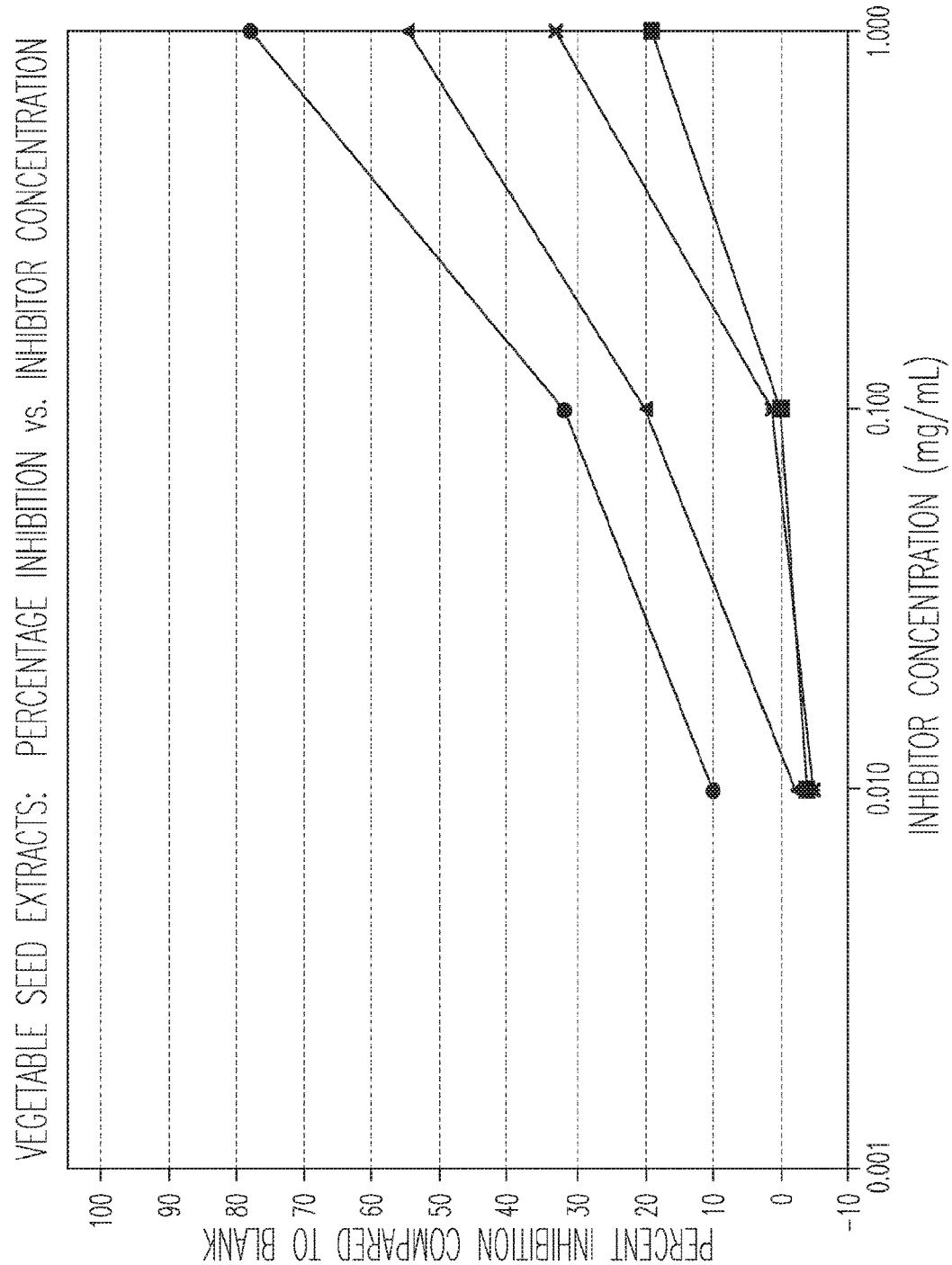
FIG. 12. Percent inhibition of vegetable seed extracts.

The percentage inhibition for each material at the various concentrations is also graphed in FIGS. 11-12, which show dose-response curves for known inhibitors, fruit seed extracts, and vegetable seed extracts, respectively. All of the graphs use the same scale, which allows the curves to be easily compared. Concentration is plotted along the X-axis in a logarithmic scale from 0.001 mg/mL on the left to 1 mg/mL on the right.

The upper graph of FIG. 11 shows the inhibition of known inhibitors and commercial skin whitening products for comparative purposes with fruit seed extract inhibition results in the bottom graph. Among the known inhibitors and commercial materials, kojic acid was the strongest inhibitor followed by quercetin. These two were considerably more potent than the others. The next best inhibitor was BASF Radianskin, which was not particularly potent at high concentration, but maintained a significant amount of activity at dilute concentrations. The other known inhibitors and commercial materials were more similar and weaker. The fruit seed extracts in the lower graph of FIG. 11 showed a variety of inhibition strengths. Red raspberry and black raspberry were the strongest extracted inhibitors, and these exceeded the activity of alpha-arbutin, beta-arbutin and hydroquinone at high concentrations. Red raspberry extract from the two-hour extraction protocol was similar to the 16 h result, with slight drop in activity at the 0.1 mg/mL level and a slight increase at the 0.01 mg/mL level. Blackberry and blueberry were the next most active, along with pomegranate. Cranberry seed extract and cranberry skin extract were basically identical and less potent than the others. Finally, watermelon was the weakest inhibitor. It is possible that the ellagic acid present in the extracts is responsible for their inhibitory activity. Several seed materials showed good potential for inhibiting tyrosinase compared to hydroquinone, which is the current standard therapy for skin whitening.

The inhibition of tyrosinase by vegetable extracts is plotted in FIG. 12. For the purposes of this study, tomato is referred to as a vegetable. Tomato showed the strongest inhibition among the pure vegetable extracts and was similar to pomegranate. Broccoli and radish extracts were similar to each other and were much weaker inhibitors then tomato. The mixture of red raspberry and tomato extracts showed somewhat stronger inhibition than either of the individual extracts alone. However, the effects do not appear to be synergistic, and in fact they do not even appear to be additive.

Conclusions

The data generated during this study show potential for using seed extracts as skin whitening agents. All of the extracts tested showed at least some ability to inhibit tyrosinase, which is a key enzyme in the biosynthesis of melanin. Many of the seed extracts performed as well as known skin whitening agents in their tyrosinase inhibition activity. This activity comes from material produced after a single round of purification via extraction with 70:30 methanol/water solutions. Further rounds of purification may increase the activity of the materials in enzyme inhibition assays. While the presence of ellagic acid in several of the fruit materials was a common theme, there was a good deal of diversity between the seed materials with many unique compounds present in each. For example, the molecule sulforaphane is a high value molecule found in broccoli. Melanogenesis is a complicated process that involves the action of many enzymes in addition to tyrosinase, which is just the most well known target among many. Therefore, a compound or extract that could be a potent skin-whitening agent may not be a strong inhibitor of tyrosinase.

Similar compounds or compounds with similar activities to those discussed above may be obtained from other seed materials including grape seeds, pumpkin seeds and chia seeds. The grape seeds in particular are interesting because they likely contain the compound resveratrol, which is a known tyrosinase inhibitor.

Microwave-assisted extractions of select seed powders may be employed.

HPLC coupled with MS (mass spectrometry) is useful to identify the major compounds in extracts.

Example V

Ellagitannins and other hydrolyzable tannins in raspberry seed extract powder were characterized by MALDI-TOF Mass Spectrometry.

Materials and Methods

Matrix-Assisted Laser Desorption/Ionization Time-of-Flight Mass Spectrometry

Mass spectra were collected on a Bruker MicroflexLRF MALDI-TOF mass spectrometer (Billerica, MA) equipped with delayed extraction and a N2 laser (337 nm). Spectra were collected in negative reflectron mode using an accelerating voltage of 25.0 kV and a reflectron voltage of 26.5 kV. Spectra are the sum of <3000 shots. Spectra were calibrated with bradykinin (Sigma, St. Louis, MO) as an external standard. 2, 5-dihydroxybenzoic acid (Aldrich, Milwaukee, WI) solubilized in ethanol (50 mg/mL) was used as a matrix. Sample was mixed with the matrix solution at volumetric ratios of 1:2 and the mixture (1 NL) was deposited on a stainless steel target. All results are reported as a deprotonated mass [M-H]−.

Figure 13:
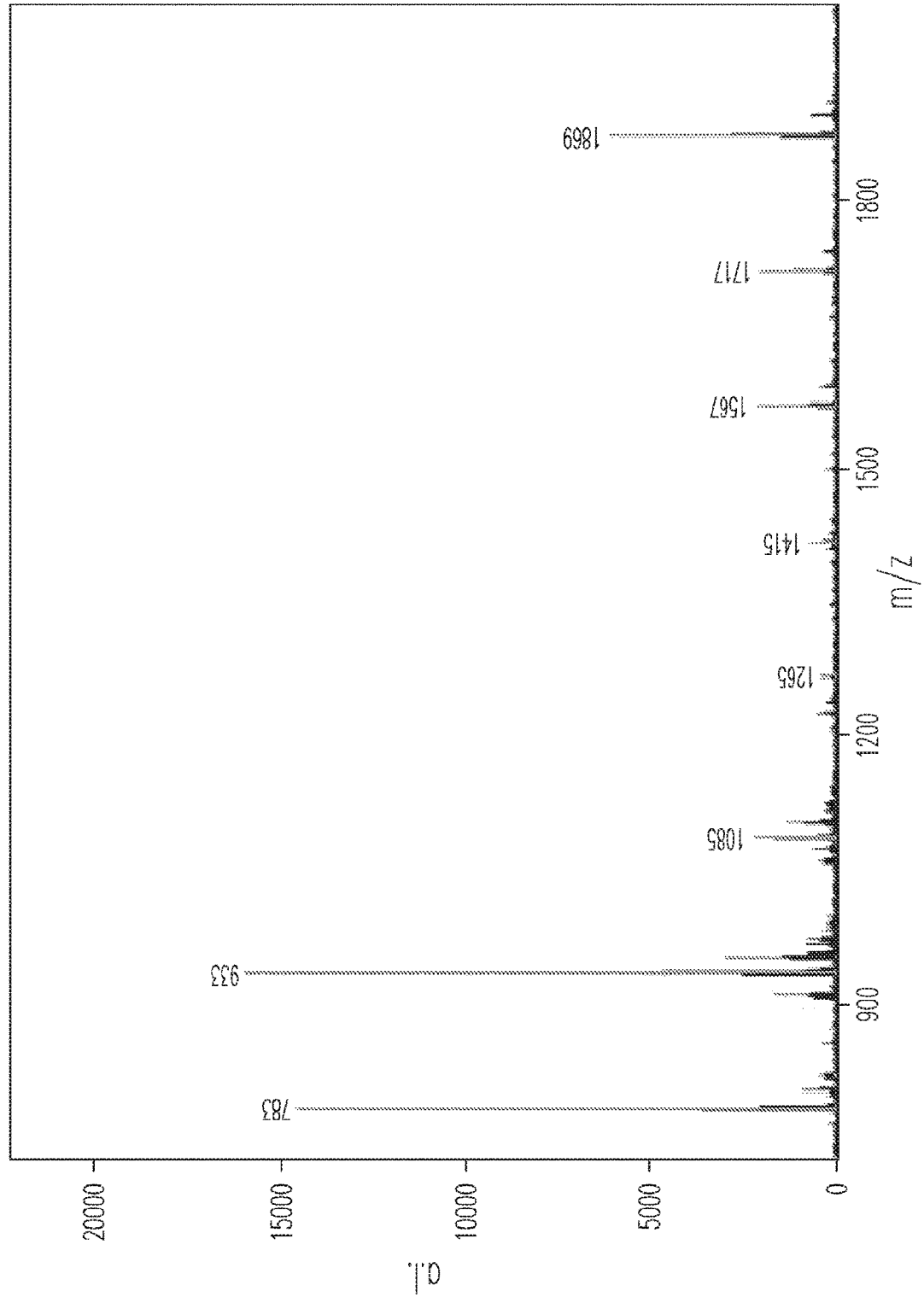
FIG. 13. Negative reflectron mode matrix-assisted laser desorption/ionization time-of-flight mass spectra of ellagitannins and other hydrolyzable tannins in raspberry seed extract powder detected as [M-H]–.

(1985, 1986a and 1986b). Tentative structural assignments of compounds are based on substitutions with glucose, gallagic acid, hexahydroxydiphenoyl (HHDP), gallic acid and dehydrodigalloyl acid (DHDG) (Afaq et al.; Martin et al., 2009). While MALDI-TOF MS is able distinguish molecular weight differences due to degree of polymerization and structural substitutions, it does not have the ability to assign specific stereochemistry to a molecule. Results (FIG. 13 and Table 5) indicated that raspberry seed extract powder contained masses with a similar distribution to those describe by Martin et al. (2009) and Kula et al. (2016).

The results demonstrate the presence of nine specific ellagitannins in the extract. These include ellagitannins that have:

1) a glucose core with two HHDP (hexahydroxydiphenoyl) groups, which has a mass of 784 amu (atomic mass units),
2) a glucose core with one gallagosyl group and one galloyl group, which has a mass of 934 amu,
3) a glucose core with one gallagosyl group and one HHDP group, which has a mass of 1084 amu,
4) a glucose core with two gallagosyl groups, which has a mass of 1086 amu,
5) two glucose cores with one gallagosyl group and two galloyl groups, which has a mass of 1266 amu,
6) two glucose cores with one gallagosyl group, one galloyl group, and one DHDG (dihydrodigalloyl) group, which has a mass of 1416 amu,
7) two glucose cores with three HHDP groups and one DHDG group, which has a mass of 1568 amu,
8) two glucose cores with one gallagosyl group, one HHDP group, one galloyl group, and one DHDG group, which has a mass of 1718 amu, and
9) two glucose cores with one gallagosyl group, one HHDP group, two galloyl groups, and one DHDG group, which has a mass of 1870 amu.

TABLE 5

Matrix-assisted laser desorption/ionization time-of-flight mass spectrometry (MALDI-TOF MS) of ellagitannins and other hydrolyzable tannins in raspberry seed extract powder.

| Ellagitannin & Hydrolyzable tannins | Glucosyl | Gallagosyl | HHDP | Galloyl | DHDG | Expected Mass [M-H] | Observed Mass [M-H] |
|---|---|---|---|---|---|---|---|
| | 1 | 0 | 2 | 0 | 0 | 783 | 783 |
| | 1 | 1 | 0 | 1 | 0 | 933 | 933 |
| | 1 | 1 | 1 | 0 | 0 | 1083 | 1083 |
| | 1 | 2 | 0 | 0 | 0 | 1085 | 1085 |
| Dimers | 2 | 1 | 0 | 2 | 0 | 1265 | 1265 |
| | 2 | 1 | 0 | 1 | 1 | 1415 | 1415 |
| | 2 | 0 | 3 | 0 | 1 | 1567 | 1567 |
| | 2 | 1 | 1 | 1 | 1 | 1717 | 1717 |
| | 2 | 1 | 1 | 2 | 1 | 1869 | 1869 |

HHDP: Hexahydroxydiphenoyl, DHDG: Dehydrodigalloyl.

Results and Discussion

Characterization of Ellagitannins and Other Oligomeric Hydrolyzable Tannin Distribution by Matrix-Assisted Laser Desorption/Ionization-Time of Flight Mass Spectrometry (MALDI-TOF MS)

MALDI-TOF MS was used to identify the monomeric and oligomeric hydrolysable tannins in the sample. The predicted masses are based on structural features of ellagitannin and gallotannin chemistry described by Tanaka et al.

Example VI

A skin safety study was conducted. The initial extracts in aqueous and alcoholic solution were used for preliminary testing to determine whether they may cause irritation or skin sensitization. The test method applied a few drops of the extract to the same spot on the skin once daily. On the following day they skin was observed and evaluated using the following scale for signs of redness irritation. Subjects self reported. The aqueous form of the extract was used for two subjects (one male and one female) and the alcoholic form of the extract was used by one subject (a female).

Dermal Scoring Scale
0 No visible skin reaction
+ Barely perceptible erythema
1+ Mild erythema
2+ Well defined erythema
3+ Erythema and edema
4+ Erythema and edema with vesiculation The following charts are the scores for a 30 day period. No irritation, redness or skin sensitization was reported.

TABLE 6

| TEST MATERIAL SUBJECT NUMBER | SKIN LIGHTENING EXTRACTS DAILY INDUCTION SCORES | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 1 | 0 | 0 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 | 0 | 0 | 0 |

| TEST MATERIAL SUBJECT NUMBER | SKIN LIGHTENING EXTRACTS DAILY INDUCTION SCORES | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| 1 | 0 | 0 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 | 0 | 0 | 0 |
| 3 | 0 | 0 | 0 | 0 | 0 | 0 | 10 | 0 | 0 | 0 | 0 | 0 | 0 | 0 | 0 |

Example VII

Asian or Indian subjects age 35-65 with a desire to lighten their skin, with skin type Fitz III—V, apply a formulation having an extract described above (RSE) are followed for 6 weeks. The effect of the formulation on skin lightening is assessed using chromameter assessments and expert visual assessments at Week 0 (baseline), Week 3 and Week 6.

Chromameter® Assessment of Skin Tone

Figure 14:
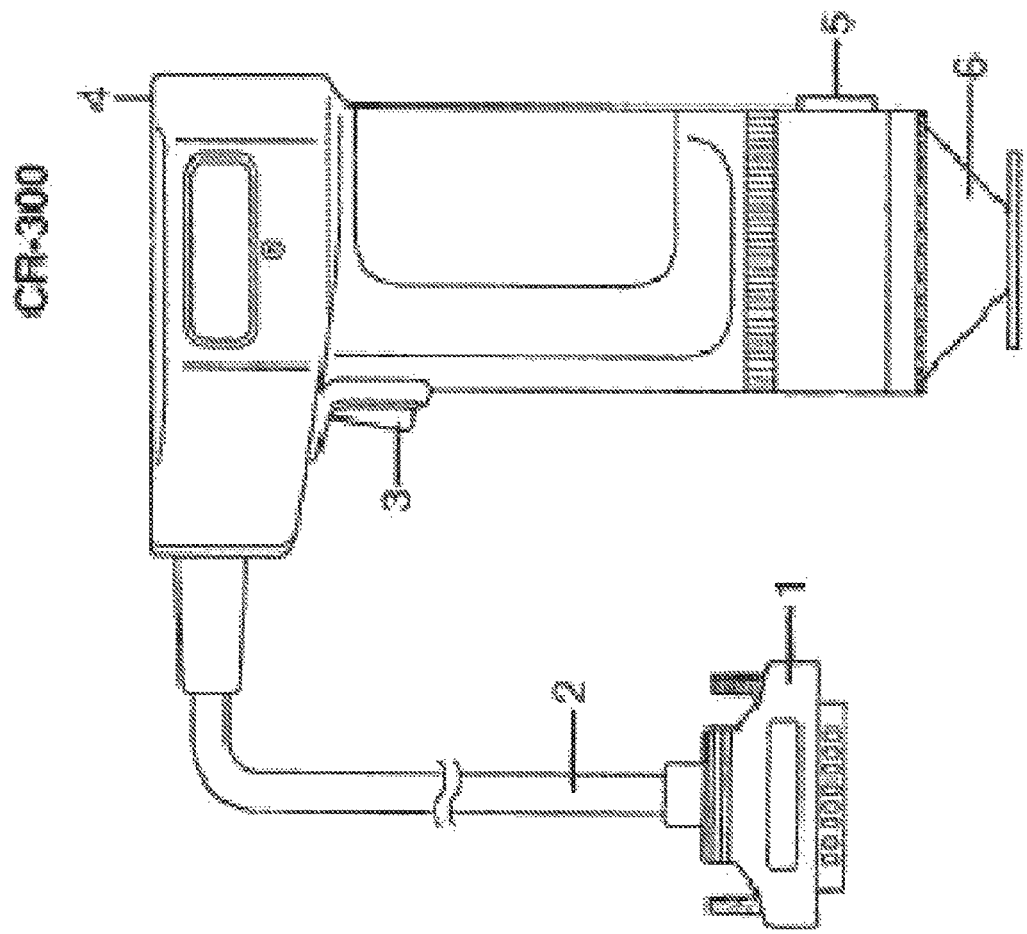
FIG. 14. Exemplary chromameter.

Instrumental measurements of skin tone were performed using a Chromameter CR300® (Courage and Khazaka, Germany) on the skin (FIG. 14). The measuring head of the CR-300 uses diffuse illumination/0° viewing geometry. A pulsed xenon arc (PXA) lamp inside a mixing chamber provides diffuse, uniform lighting over the 8 mm-diameter specimen area. Only the light reflected perpendicular to the specimen surface is collected by the optical-fiber cable for color analysis.

The instrument measures the amount of light reflected from the skin and quantifies this into a numerical value using the L*a*b* colour scale, where L*(100) equates to total white and L*(0) equates to total black. The instrument was allowed to warm up for 30 minutes prior to use. Readings were taken on the right and left side of the upper cheek, cheek bone area. L* values were recorded and analysed.

Other Analyses

Testing will take place amongst the patients, with application to solar lentigines of the face twice a day for 8 weeks. Pictures are taken before and after 8 weeks and patients fill out a questionnaire regarding patient experience (subjective safety/efficacy/ease of use/adverse events) and overall comments/satisfaction. The study controls the location of lesions (example cheek bones, forehead, cheeks, etc.) and sun exposure during the evaluation process.

Example VIII

Different solvents were tested with raspberry seed extract (RSE) (FIG. 15). The solubility data shows the relative efficiency of various solvents in solubilizing the solid extract particles. Solvents with higher efficiencies can be employed in a cosmetic formulation so that the active agent is available to penetrate the skin. The study included a second step in an attempt to solubilize the entire particle. However, since the solution from the initial solubility step does include the active agent, insoluble particles can be filtered away rather than using a second solvent.

In addition, solid raspberry seed extract (0.500 g) was combined with methanol (5 mL), the mixture was agitated, and a white colored precipitate (0.057 g) was separated from a red solution of methanol. Evaporating the methanol under vacuum gave a red foam (0.443 g) that was crushed to a free flowing powder. The white colored precipitate was highly insoluble in typical solvents. The material from the methanol fraction was highly soluble in both methanol and DMSO. That material was tested in the enzyme assay in triplicate and found it to be of equivalent potency to the original extract. Thus, the insoluble material can be removed without decreasing activity. Removal of the insoluble portion also makes the extract much more soluble and the active material appears to be less hygroscopic after insoluble materials are removed, which makes handling easier.

REFERENCES

Tanaka T, Nonaka G, Nishioka I. Punicafolin, an ellagitannin from the leaves of punica granatum. *Phytochem.* 1985; 24:2075-2078.

Tanaka T, Nonaka G, Nishioka I. Tannins and related compounds: Revision of the structures of punicalin and punicalagin, and isolation and characterization of 2-o-galloylpunicalin from the bark of punica granatum I. *Chem. Pharm. Bull.* 1986a; 34:650-655

Tanaka T, Nonaka G, Nishioka I. Isolation and characterization of novel ellagitannins, puicacorteins a, b, c, and d and punigluconin from the bark of punica granatum I. *Chem. Pharm. Bull.* 1986b; 34:656-663

Afaq F, Saleem M, Krueger C, Reed J, Mukhtar H. Anthocyanin and hyrolyzable tannin-rich pomegranate Martin K R, Krueger C G, Rodriguez G, Dreher M, Reed J D. Development of a novel pomegranate standard and new method for the quantitative measurement of pomegranate polyphenols. J Agric Food Chem. 2009; 89:157-62. Kula, M. Majdan M, Glod D. Krauze-Baranowska M. Phenolic composition of fruits from different cultivars of red and black raspberries grown in Poland. Journal of Food Composition and Analysis. 2016; 52: 74-82.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to isolate ellagic acid or ellagitannin, comprising: a) incubating a mechanically pressed raspberry, blackberry or blueberry seed extract powder and a water-C1-C4 alcohol mix to provide a mixture, wherein the extract powder has 10% or less seed oils as a result of the mechanical pressing; b) filtering the mixture; and c) separating the filtrate to provide a fraction that is enhanced in ellagic acid or ellagitannin, wherein the fraction has at least 10 mg ellagic acid per gram of seed, wherein the water is at a pH greater than 8.

2. The method of claim 1 wherein the C1-C4 alcohol is propanol, butanol, ethanol or methanol.

3. The method of claim 2 wherein the C1-C4 alcohol mix comprises 70:30 methanol:water.

4. The method of claim 1 wherein the fraction comprises an amount of ellagic acid or ellagitannin that inhibits eumelanin or pheomelanin production in human skin.

5. The method of claim 1 further comprising removing the solvent from the filtrate.

6. The method of claim 1 wherein the separation includes subjecting the filtrate to separation on a C8 column, to separation on a C18 solid phase extraction column or to separation on an ion exchange chromatography column, or any combination thereof.

7. The method of claim 1 wherein the separation includes subjecting the filtrate to high pressure liquid chromatography.

8. The method of claim 1 wherein the powder is a red raspberry seed extract powder.

9. The method of claim 1 wherein the powder is a black raspberry seed extract powder.

10. The method of claim 1 wherein the powder comprises about 10 to about 14 mg ellagic acid per gram of seed.

11. A method to isolate ellagic acid or ellagitannin, consisting of: a) combining a mechanically pressed raspberry, blackberry or blueberry seed extract powder and water-methanol to provide a mixture, wherein the extract powder has 10% or less seed oils as a result of the mechanical pressing; and b) separating the mixture using chromatography to provide a fraction that is enhanced in ellagic acid or ellagitannin, wherein the separating occurs on a C8 column, a C18 solid phase extraction column or an ion exchange chromatography column, or any combination thereof, wherein the water is at a pH greater than 8.

* * * * *